(12) United States Patent
Mohammadimasoudi et al.

(10) Patent No.: US 11,513,117 B2
(45) Date of Patent: Nov. 29, 2022

(54) SYSTEM FOR DETECTING A TARGET MATERIAL IN A SAMPLE USING LIQUID CRYSTALS

(71) Applicants: Mohammad Mohammadimasoudi, Tehran (IR); Mohamadreza Gholaminezhadshemirani, Tehran (IR); Ali Goudarzi, Tehran (IR); mahboubeh Esmaeilpour, Tehran (IR); Hosein Shahsavarani, Tehran (IR); Ezeddin Mohajerani, Tehran (IR); ALi Poorkhalil, Tehran (IR)

(72) Inventors: Mohammad Mohammadimasoudi, Tehran (IR); Mohamadreza Gholaminezhadshemirani, Tehran (IR); Ali Goudarzi, Tehran (IR); mahboubeh Esmaeilpour, Tehran (IR); Hosein Shahsavarani, Tehran (IR); Ezeddin Mohajerani, Tehran (IR); ALi Poorkhalil, Tehran (IR)

(73) Assignees: UNIVERSITY OF TEHRAN, Tehran (IR); Mohammad Mohammadimasoudi, Tehran (IR)

( * ) Notice: Subject to any disclaimer, the term of this patent is extended or adjusted under 35 U.S.C. 154(b) by 0 days.

(21) Appl. No.: 17/723,744

(22) Filed: Apr. 19, 2022

(65) Prior Publication Data
US 2022/0299507 A1    Sep. 22, 2022

Related U.S. Application Data

(63) Continuation-in-part of application No. PCT/IB2022/050580, filed on Jan. 24, 2022.
(Continued)

(51) Int. Cl.
*G01N 33/543*   (2006.01)
*G01N 21/33*    (2006.01)
*G01N 33/569*   (2006.01)

(52) U.S. Cl.
CPC ....... *G01N 33/54373* (2013.01); *G01N 21/33* (2013.01); *G01N 33/56983* (2013.01); *G01N 2333/165* (2013.01)

(58) Field of Classification Search
CPC ............. G01N 33/54373; G01N 21/33; G01N 33/56983; G01N 2333/165
See application file for complete search history.

(56) References Cited

U.S. PATENT DOCUMENTS

2004/0009729 A1* 1/2004 Hill ...................... D03D 1/0088
442/181

OTHER PUBLICATIONS

Gao et al, "Epidermal photonic devices for quantitative imaging of temperature and thermal transport characteristics of the skin" Nat. Commun. 5:4938 doi: 10.1038/ncomms5938, pp. 1-10 (2014). (Year: 2014).*

* cited by examiner

*Primary Examiner* — Dennis White
(74) *Attorney, Agent, or Firm* — Bajwa IP Law Firm; Haris Zaheer Bajwa

(57) ABSTRACT

A system for detecting a target material in a sample. The system includes a sensor, a light source, an image-capturing device, two linear-crossed polarizers including a first polarizer and a second polarizer, and a processing unit. The sensor is configured to place the sample thereon and includes a fabric impregnated with liquid crystals (LCs). The light source is configured to transmit a beam of light through a path passing from the first polarizer, the sensor, and the second polarizer. The image-capturing device is configured to capture an image of a surface of the second polarizer. The (Continued)

image contains a pattern formed by orientations of LCs corresponding to the sample. The processing unit is configured to detect a presence of the target material in the sample by analyzing the captured image.

20 Claims, 33 Drawing Sheets

Related U.S. Application Data

(60) Provisional application No. 63/143,961, filed on Feb. 1, 2021.

204

SYSTEM FOR DETECTING A TARGET MATERIAL IN A SAMPLE USING LIQUID CRYSTALS

CROSS-REFERENCE TO RELATED APPLICATION

This application is a continuation-in-part of International Patent Application PCT/IB2022/050580, filed on Jan. 24, 2022, and entitled "SYSTEM FOR DETECTING A TARGET MATERIAL IN A SAMPLE USING LIQUID CRYSTALS", which takes priority from U.S. Provisional Patent Application Ser. No. 63/143,961, filed on Feb. 1, 2021, and entitled "SENSORS BASED ON TEXTILE IMPREGNATED WITH LIQUID CRYSTAL", which are both incorporated herein by reference in their entirety.

TECHNICAL FIELD

The present disclosure generally relates to a system and a method for detecting and/or quantifying a target material in a sample utilizing liquid crystals, and more particularly, a system and a method to detect and/or quantify a target material in a sample by analyzing patterns formed by orientations of liquid crystals responsive to interaction of liquid crystals with the sample.

BACKGROUND

A sensor is a device that detects changes in an environment and converts the changes into data. Changes in an environment may include changes in pH value, materials' concentration, flow of different gases, etc. Detection and quantification of these changes in an environment is crucial for collecting knowledge from the environment. Biomaterials such as viruses and bacteria are capable of duplicating in a short period of time and spreading infection into host cells. Detecting biomaterials in early stages of infection is vital for hindering high-speed spread of viruses and bacteria in new hosts.

Different sensors are used to detect and quantify various changes in an environment, such as biosensors, thermal sensors, pressure sensors, gas sensors, etc. These sensors use different technologies to identify changes and convert these changes into data. Liquid crystals (LCs) with properties between conventional liquids and solid crystals are used in sensors. LCs may flow like a liquid while molecules of LCs are oriented in a crystal shape. LCs are organic, rod-shaped anisotropic materials which are oriented in a parallel configuration. LCs reorient in contact with different materials and have a distinct orientation pattern for each material, which makes LCs appropriate sensing agents for a wide range of target analytes. However, labels or markers are required in current sensors using LCs to amplify sensor responses. Labels such as fluorescent materials interact with analytes to amplify responses of sensors. Using fluorescent materials as a label is expensive and requires sophisticated equipment.

There is, therefore, a need for a cost-effective, user-friendly, label-free, and fast LCs-based sensor, system, and method to use thereof to detect materials such as viruses, bacteria, gases, etc.

SUMMARY

This summary is intended to provide an overview of the subject matter of this patent, and is not intended to identify essential elements or key elements of the subject matter, nor is it intended to be used to determine the scope of the claimed implementations. The proper scope of this patent may be ascertained from the claims set forth below in view of the detailed description below and the drawings.

According to one or more exemplary embodiments, the present disclosure is directed to a system for detecting a target material in a sample. An exemplary system may include a sensor that may be configured to place an exemplary sample thereon, a light source, an image-capturing device, two linear crossed polarizers, and a processing unit. In an exemplary embodiment, an exemplary sensor may include a fabric and liquid crystals (LCs). An exemplary fabric may include an array of pixels in which each respective pixel may include a square hole that may be formed by texture of an exemplary fabric. Exemplary LCs may be impregnated into an exemplary array of pixels. In an exemplary embodiment, exemplary two linear crossed polarizers may include a first polarizer may be placed between an exemplary light source and an exemplary sensor and a second polarizer may be placed between an exemplary sensor and an exemplary image-capturing device. In an exemplary embodiment, an exemplary processing unit may be electrically connected to an exemplary light source and an exemplary image-capturing device. In an exemplary embodiment, an exemplary processing unit may include a memory having processor-readable instructions stored therein and a processor. In an exemplary embodiment, the processor may be configured to access an exemplary memory and may execute exemplary processor-readable instructions. In an exemplary embodiment, the executed processor-readable instructions by an exemplary processor may configure an exemplary processor to perform a method. In an exemplary embodiment, an exemplary method may include transmitting, utilizing the light source, a light beam through a path. An exemplary path may include an exemplary first polarizer, an exemplary sensor, and an exemplary second polarizer. An exemplary method may further include capturing, utilizing an exemplary image-capturing device, an image from a surface of an exemplary second polarizer. An exemplary image may include a pattern formed by orientations of the LCs associated with an exemplary sample placed on an exemplary sensor. An exemplary method may further include detecting a presence of an exemplary target material in an exemplary sample by analyzing an exemplary pattern may be formed by orientations of exemplary LCs responsive to placing an exemplary sample on an exemplary sensor.

In an exemplary embodiment, analyzing an exemplary pattern formed by orientations of exemplary LCs may include comparing an exemplary pattern formed by orientations of exemplary LCs with a set of reference patterns of an exemplary target material and detecting an exemplary presence of an exemplary target material in an exemplary sample responsive to an exemplary pattern formed by orientations of exemplary LCs being similar to a reference pattern of an exemplary set of reference patterns with a similarity of more than 80%. In an exemplary embodiment, an exemplary similarity of more than 80% may include orientations of exemplary LCs associated with at least 80% pixels of an exemplary array of pixels may be the same in an exemplary reference pattern and in an exemplary pattern formed by orientations of exemplary LC's.

In an exemplary embodiment, an exemplary set of reference patterns of an exemplary target material may include a set of images may be captured from an exemplary surface of an exemplary second polarizer respective to a set of formed orientations of exemplary LCs responsive to placing a respective set of reference samples containing a respective set of amounts of an exemplary target material on an exemplary sensor.

In an exemplary embodiment, analyzing an exemplary pattern formed by orientations of exemplary LCs may include generating an array of vectors for each reference pattern of an exemplary set of reference patterns by determining a direction for each respective vector corresponding to an orientation of LCs in a respective pixel of an exemplary array of pixels based on a color spectrum of an exemplary respective pixel in an exemplary reference pattern, generating a sample array of vectors for an exemplary pattern formed by orientations of LCs in an exemplary sample by determining a direction for each respective vector corresponding to an orientation of LCs in a respective pixel of an exemplary array of pixels based on a color spectrum of an exemplary respective pixel in an exemplary pattern may be formed by orientations of LCs in an exemplary sample, comparing an exemplary sample array of vectors with an exemplary array of vectors of each reference pattern of an exemplary set of reference patterns, and determining an exemplary presence of an exemplary target material in an exemplary sample responsive to a direction of each vector of an exemplary sample array of vectors being the same to a direction of each respective vector of an exemplary array of vectors of a first reference pattern of an exemplary set of reference patterns.

In an exemplary embodiment, an exemplary method may further include determining an amount of an exemplary target material in an exemplary sample by determining an exemplary amount of an exemplary target material in an exemplary sample equal to a first amount of an exemplary target material of an exemplary set of amounts of an exemplary target material, an exemplary first reference pattern may be corresponding to a reference sample containing an exemplary first amount of an exemplary target material.

In an exemplary embodiment, an exemplary first polarizer and an exemplary second polarizer may be linear crossed polarizers. In an exemplary embodiment, an exemplary first polarizer may have 90 degree difference in light transmittance respective to an exemplary second polarizer.

In an exemplary embodiment, analyzing an exemplary pattern formed by orientations of exemplary LCs may include analyzing an exemplary pattern formed by orientations of exemplary LCs after placing an exemplary sample on an exemplary sensor for a time period of 10 seconds to 10 minutes.

In an exemplary embodiment, an exemplary sensor may include LCs with a volume in a range of 0.0001 µL to 0.0005 µL that may be impregnated into each pixel of an exemplary array of pixels.

In an exemplary embodiment, each pixel of an exemplary array of pixels may include a volume in a range of 0.0001 µL to 0.003 µL of an exemplary sample that may be placed on an exemplary sensor.

In an exemplary embodiment, transmitting an exemplary light beam may include transmitting an exemplary light beam with a wavelength within a range of UV-Visible wavelength.

In an exemplary embodiment, LCs impregnated into an exemplary array of pixels may include at least one of thermotropic LCs, lyotropic LCs, and combinations thereof. In an exemplary embodiment, an exemplary thermotropic LCs may include at least one of nematic LCs, smectic LCs, chiral phases, twisted nematic LCs, discotic LCs, conic LCs, and combinations thereof.

In an exemplary embodiment, an exemplary sensor may further include a holder placed around an exemplary fabric. In an exemplary embodiment, an exemplary holder may be made of at least one of iron, galvanized steel, polymethylmethacrylate, wood, and combinations thereof.

In an exemplary embodiment, an exemplary sensor may further include a binding agent. In an exemplary embodiment, the binding agent may be added to each respective pixel of the array of pixels. In an exemplary embodiment, the binding agent may be configured to interact with an exemplary target material in an exemplary sample, an exemplary binding agent may include at least one of diethanolamine, hexavalent vaccine, pentavalent vaccine, aptamers, and combinations thereof.

In an exemplary embodiment, the sample may include one of a sputum sample, a blood sample, and a nasal mucosa sample acquired from a person who is suspected to be infected by COVID-19 virus. In an exemplary embodiment, detecting the presence of the target material in the sample by analyzing the pattern formed by orientations of the LCs may include detecting a COVID-19 infection in the sample by analyzing the pattern formed by orientations of the LCs.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1A:
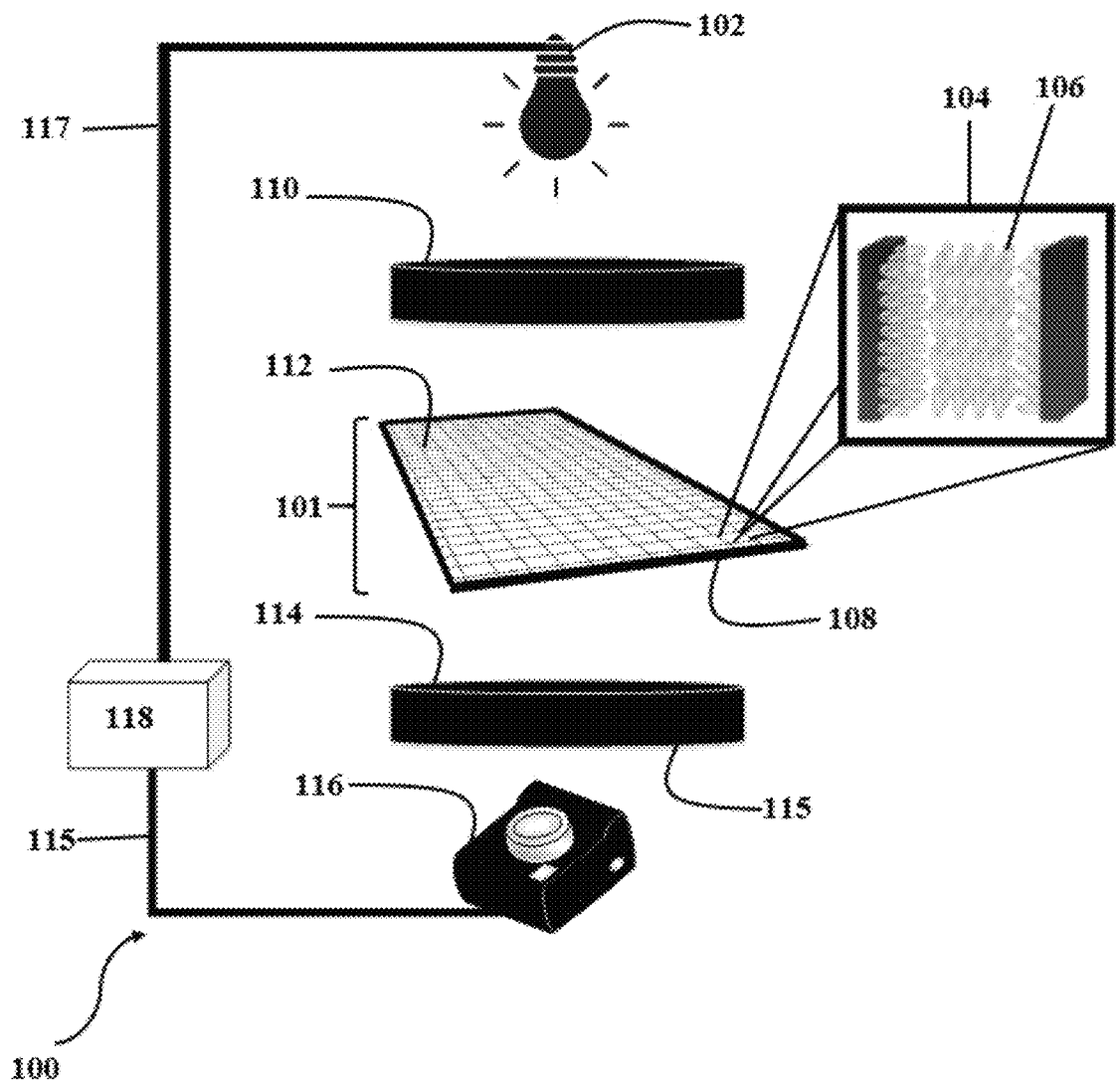
FIG. 1A illustrates a schematic view of an exemplary system for detecting a target material in an exemplary sample, consistent with one or more exemplary embodiments of the present disclosure.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The novel features which are believed to be characteristic of the present disclosure, as to its structure, organization, use and method of operation, together with further objectives and advantages thereof, will be better understood from the following discussion. In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

The present disclosure is directed to exemplary embodiments of a system and a method to detect and/or quantify a target material in a sample. In an exemplary embodiment, a presence of a target material (or target species) may be detected in a sample utilizing exemplary method and/or system disclosed herein. In an exemplary embodiment, a concentration or amount of a target material may be detected utilizing exemplary method and/or system. In an exemplary embodiment, an exemplary target material may include a biological or chemical species. In an exemplary embodiment, an exemplary target material may include at least one of a gas molecule, a liquid molecule, and combinations thereof. In an exemplary embodiment, an exemplary target material may include a biological molecule, a gas, a molecule hovering in the air, a molecule dispersing in a liquid, an alcohol, a molecule dissolved in a liquid, and combinations thereof. In an exemplary embodiment, exemplary biological or chemical species may include at least one of a biological or chemical species. In an exemplary embodiment, an exemplary gas may include at least one of carbon monoxide, nitrogen, argon, carbon dioxide, and combinations thereof. In an exemplary embodiment, an exemplary biological molecule may include at least one of a polysaccharide, a lipid, a nucleic acid, an antibody, a protein, a carbohydrate, a virus, an antigen, a pathogen, a DNA, a RNA, and combinations thereof.

In an exemplary embodiment, an exemplary biological molecule may include at least one of herpes virus, influenza A, influenza B, and coronavirus, for example, COVID-19. In an exemplary embodiment, an exemplary sample may include a tissue or a fluid from a human, animal, or plant. In an exemplary embodiment, an exemplary sample may be at least one of saliva, mucus, blood, blood plasma, and urine. In an exemplary embodiment, an exemplary target material may include a contamination in a sample to be identified and/or quantified. In an exemplary embodiment, an exemplary target material may include methanol contamination in alcoholic drinks.

In an exemplary embodiment, exemplary method and system may be utilized for diagnosing a subject as having a disorder, wherein a presence of a target biological molecule in the sample may indicate a presence of the disorder. In an exemplary embodiment, the disorder may be an infectious disease. Additionally, an exemplary disease may be dengue fever, AIDS, hepatitis, sexually transmitted diseases, antibiotic resistance, and the like. Furthermore, in an exemplary embodiment, exemplary system and/or method disclosed here may be utilized for detecting at least one of vibration, acceleration, and flow of molecules. In an exemplary embodiment, exemplary system and/or method disclosed here may be utilized for detecting at least one of temperature, pH, ions such as $H^+$, concentration of ions or molecules, and combinations thereof.

An exemplary system may include a senor, two polarizers, an image-capturing device, a light source, and a processing unit. An exemplary sensor may be placed between exemplary two polarizers. An exemplary first polarizer may be placed between an exemplary light source and an exemplary sensor. An exemplary second polarizer may be placed between an exemplary image-capturing device and an exemplary sensor. Exemplary polarizers may be linear crossed polarizers that may produce linear polarized light. In an exemplary embodiment, as used herein, linear polarized light may refer to a polarized light with one transition direction produced from unpolarized light. When the transmission direction of exemplary two linear crossed polarizers are placed with an orthogonal orientation, exemplary two polarizers may eliminate all light and therefore, no light may be transmitted from an exemplary second polarizer.

An exemplary sensor may include a fabric impregnated with liquid crystals (LCs) and a holder. In an exemplary embodiment, an exemplary holder may be placed around an exemplary fabric to fix an exemplary fabric in a plane surface with no wrinkles. An exemplary holder may include a plate with a plurality of open-ended holes on an exemplary plate. In an exemplary embodiment, to fix an exemplary fabric on an exemplary plate, a clamp and/or an adhesive substance may be used. In another exemplary embodiment, an exemplary holder may include a hoop and a frame to fix an exemplary fabric. In an exemplary embodiment, an exemplary holder may include a pair of concentric circular or elliptical rings (hoop and frame) in which a larger ring (frame) may include a tightening device, in a form of a metal screw to fix an exemplary hoop and an exemplary frame together. An exemplary fabric may be made of at least one of polyester, rayon, linen, nylon, silk, and combinations thereof with a thickness in a range of 10 μm to 10 μm. An exemplary fabric may include an array of pixels in which each respective pixel may include a square hole may be formed by texture of an exemplary fabric. The term "pixel" as used herein may refer to an exemplary square hole created by warp and weft of an exemplary fabric. In an exemplary embodiment, an exemplary fabric may be impregnated with LCs. In an exemplary embodiment, an exemplary warp and weft of an exemplary fabric may keep exemplary LCs inside exemplary square holes of an exemplary fabric.

An exemplary fabric may be impregnated with LCs at a volume in a range of 0.0001 μL to 0.0005 μL into each pixel of an exemplary array of pixels of an exemplary fabric. In an exemplary embodiment, LCs are a category of materials with properties between conventional liquids and solid crystals. Exemplary LCs may include at least one of thermotropic LCs, lyotropic LCs, and combinations thereof. In an exemplary embodiment, the thermotropic LCs may include at least one of nematic LCs, smectic LCs, chiral phases, twisted nematic LCs, discotic LCs, conic LCs, and combinations thereof. LCs may be aligned homeotropically when air may be in contact with LCs from top and bottom of an exemplary sensor.

An exemplary sample with a volume in a range of 0.0001 µL to 0.003 µL for each pixel of an exemplary array of pixels of an exemplary fabric containing exemplary target materials may be added on an exemplary impregnated fabric with LCs utilizing a micropipette. Orientations of LCs may change in contact with exemplary target materials. An exemplary light source may transmit UV-Visible light in a path through an exemplary first polarizer, an exemplary sensor, and an exemplary second polarizer, respectively. An exemplary light transmitted from an exemplary light source may path through an exemplary sensor containing LCs with a specific orientation respective to exemplary target materials. An exemplary light may refract due to orientations of LCs in contact with target materials. An exemplary refraction may induce a specific pattern for each respective target material. An exemplary image-capturing device may take a picture of a pattern formed by orientations of LCs in contact with target materials. Exemplary pictures captured utilizing an exemplary image-capturing device may be used to detect and/or quantify an exemplary target material in an exemplary sample. Exemplary target materials may be detected by analyzing exemplary pictures by a human and/or a processing unit. An exemplary processing unit may include a memory and a processor to analyze exemplary pictures may be captured by an exemplary image-capturing device. An exemplary memory may contain processor-readable instructions to give instructions to an exemplary processor. An exemplary processing unit may be electrically connected to an exemplary image-capturing device and an exemplary light source. An exemplary processing unit may be responsible for controlling light source to transmit light, an exemplary image-capturing device to take pictures of a surface of an exemplary second polarizer, and detect and/or quantify a target material in a sample. In an exemplary embodiment, each picture may include a pattern formed by orientations of exemplary LCs. In an exemplary embodiment, an exemplary processing unit may be a computer system using a machine learning technique for analysis. A human and/or an exemplary processing unit may compare the produced pattern of an exemplary sample with a set of reference patterns. An exemplary set of reference patterns may be formed by orientations of LCs in a set of reference samples while analyzing an exemplary set of reference samples utilizing an exemplary system. A target material may be detected in an exemplary sample when an exemplary pattern of an exemplary sample may be the same as a reference pattern of an exemplary set of reference patterns.

FIG. 1A illustrates a schematic view of a system 100 for detecting a target material in an exemplary sample, consistent with one or more exemplary embodiments of the present disclosure. In an exemplary embodiment, system 100 may be utilized by one or more steps of method 400 illustrated herein below. In an exemplary embodiment, system 100 may be used to detect and/or quantify a target material in a sample. In an exemplary embodiment, a concentration or an amount of an exemplary target material may be detected utilizing system 100. In an exemplary embodiment, system 100 may include a senor 101, two linear crossed polarizers 110 and 114, an image-capturing device 116, a light source 102, and a processing unit 118. In an exemplary embodiment, exemplary two linear crossed polarizers may include a first polarizer 110 and a second polarizer 114.

In an exemplary embodiment, first polarizer 110 may be placed between sensor 101 and light source 102. In an exemplary embodiment, second polarizer 114 may be placed between sensor 101 and image-capturing device 116. In an exemplary embodiment, processing unit 118 may be electrically connected to light source 102 utilizing electrical line 117 or via a wireless connection, for example, a Bluetooth module. In an exemplary embodiment, processing unit 118 may be electrically connected to image-capturing device 116 utilizing electrical line 115 or via a wireless connection, for example, a Bluetooth module. In an exemplary embodiment, processing unit 118 may be utilized for controlling light source 102 to transmit light, image-capturing device 116 to take pictures of a surface of second polarizer 114, and detect and/or quantify an exemplary target material in sample 120. In an exemplary embodiment, second polarizer 114 may be placed at a distance in a range of 0.2 cm to 30 cm from sensor 101. In an exemplary embodiment, light source 102 may transmit a light beam with a wavelength within a range of UV-Visible wavelength in a path through first polarizer 110, sensor 101, and second polarizer 114, respectively. In an exemplary embodiment, light source 102 may include at least one of LED lamp, an incandescent light bulb, a cellphone light, and combinations thereof.

In an exemplary embodiment, sensor 101 may include LCs 106 and a fabric 112 fixed on a holder 108, that is, LCs 106 may be intertwined within fabric 112. In an exemplary embodiment, holder 108 may be configured to hold fabric 112 in a stretched position allowing for eliminating elasticity effect of fabric 112. In an exemplary embodiment, holder 108 may fix fabric 112 tight enough so that there may be no place for movement of fabric 112. In an exemplary embodiment, holder 108 is illustrated schematically in FIGS. 2A and 2B herein below. In an exemplary embodiment, fabric 112 may be made of at least one of polyester, rayon, linen, nylon, silk, and combinations thereof with a thickness in a range of 10 µm to 100 µm. In an exemplary embodiment, fabric 112 may include an array of pixels in which each respective pixel 104 may include a square hole that may be formed by texture of fabric 112. The term "pixel" as used herein may refer to an exemplary square hole created by warp and weft in fabric 112. In an exemplary embodiment, each respective pixel 104 of an exemplary array of pixels may include a dimension in a range of 1 µm to 600 µm.

In an exemplary embodiment, fabric 112 may be impregnated with LCs 106 utilizing a micropipette. As used herein, "impregnate" may refer to soak or saturate something with a substance. In an exemplary embodiment, an exemplary micropipette may be a device with a disposable tip for aspirating or injecting liquids on a surface or inside a vacant space. In an exemplary embodiment, after adding LCs 106 utilizing an exemplary micropipette, a disposable tip may be used to spread LCs 106 on fabric 112. In an exemplary embodiment, an exemplary disposable tip may be sterile. In an exemplary embodiment, an exemplary warp and weft of fabric 112 may keep LCs 106 inside exemplary square holes (pixels) of fabric 112. LCs 106 may be sensitive to materials that may be in contact with LCs' surfaces and LCs 106 may reorient in response to the contact with materials. In an exemplary embodiment, LCs 106 may be sensitive to an exemplary target material that may be detected and/or quantified in an exemplary sample utilizing system 100. In an exemplary embodiment, LCs 106 may include anisotropic LCs. As used herein, anisotropic may refer to a property of a material to allow the material change their orientations and react differently to external stimuli. In an exemplary embodiment, an orientation of LCs 106 may be changed responsive to a contact between an exemplary target material in an exemplary sample, placed on exemplary sensor 101, with LCs 106. In an exemplary embodiment, an orientation of anisotropic LCs may be detectable by observing a pattern formed by orientations of LCs 106 in the presence of a light beam transmitted through linear crossed polarizers 110 and 114. In an exemplary embodiment, fabric 112 may be impregnated with a volume of LCs 106 in a range of 0.01 μL to 0.1 μL. In an exemplary embodiment, fabric 112 may be impregnated with a volume of LCs 106 in a range of 0.0001 μL to 0.0005 μL put into each respective pixel 104 of an exemplary array of pixels of fabric 112. In an exemplary embodiment, LCs 106 may include at least one of thermotropic LCs, lyotropic LCs, and combinations thereof. In an exemplary embodiment, an exemplary thermotropic LCs may include at least one of nematic LCs, smectic LCs, chiral phases, twisted nematic LCs, discotic LCs, conic LCs, and combinations thereof.

In an exemplary embodiment, linear crossed polarizers 110 and 114 may produce linear polarized light. As used herein, linear polarized light may refer to a polarized light with one transition direction produced from unpolarized light. As used herein, crossed polarizers are a set of two polarizers in which the transmitted light beam of a first polarizer may have 90 degree difference with the transmitted light beam of a second polarizer. In an exemplary embodiment, an exemplary first polarizer 110 and exemplary second polarizer 114 may be linear crossed polarizers. In an exemplary embodiment, exemplary first polarizer 110 may have 90 degree difference in light transmittance respective to exemplary second polarizer 114.

In an exemplary embodiment, an unpolarized light beam may be generated by light source 102, the generated unpolarized light beam may be transmitted in a path through first polarizer 110 so that a beam of polarized light with a zero angle may be emitted from first polarizer 110 which may include a light beam in straight direction. In an exemplary embodiment, the emitted light from first polarizer 110 may pass through sensor 101 which may contain LCs 106 with homeotropic alignment. In an exemplary embodiment, the emitted light beam may pass through LCs 106 with no light refraction. In an exemplary embodiment, an exemplary light beam may pass through first polarizer 110, sensor 101, and may reach second polarizer 114. In an exemplary embodiment, second polarizer 114 may permit light beam to transfer from second polarizer 114 with 90 degree difference in direction respective to a passed direction from first polarizer 110. In an exemplary embodiment, due to 90 degree difference of transmitted light beam angle, no light, may exit from second polarizer 114 and image-capturing device 116 may take a dark photo from surface 115 of second polarizer 114. In an exemplary embodiment, image-capturing device 116 may include at least one of a camera, a camera of a cellphone, and a polarizer microscope. In another exemplary embodiment, image-capturing device 116 may be naked eyes of a human to detect patterns of LCs observable on second polarizer 114.

Figure 2A:
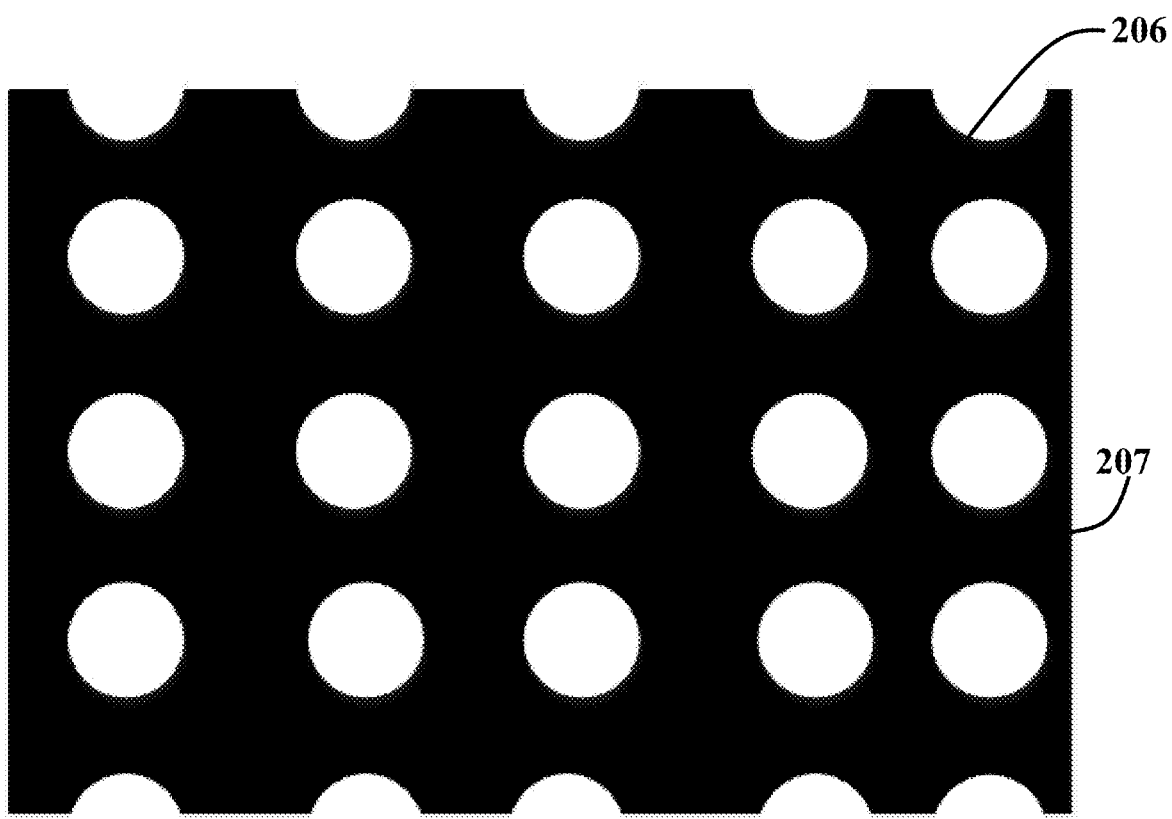
FIG. 2A illustrate a schematic view of a first exemplary structure of an exemplary holder for fixing a fabric, consistent with one or more exemplary embodiments of the present disclosure.

FIG. 2A illustrates a schematic view of a first exemplary structure of a holder 204 configured to fix fabric 112 thereon, consistent with one or more exemplary embodiments of the present disclosure. In an exemplary embodiment, holder 204 may be prepared by perforating a plate 207. In an exemplary embodiment, perforating plate 207 may include forming multiple holes on holder 204 to let light beams pass through holder 204. In an exemplary embodiment, plate 207 may be made of at least one of iron, galvanized steel, polymethylmethacrylate, wood, and combinations thereof. In an exemplary embodiment, plate 207 may include a plurality of open-ended holes 206 configured to let a light beam transmitted from light source 102, passed through sensor 101, and reached second polarizer 114.

Figure 2B:
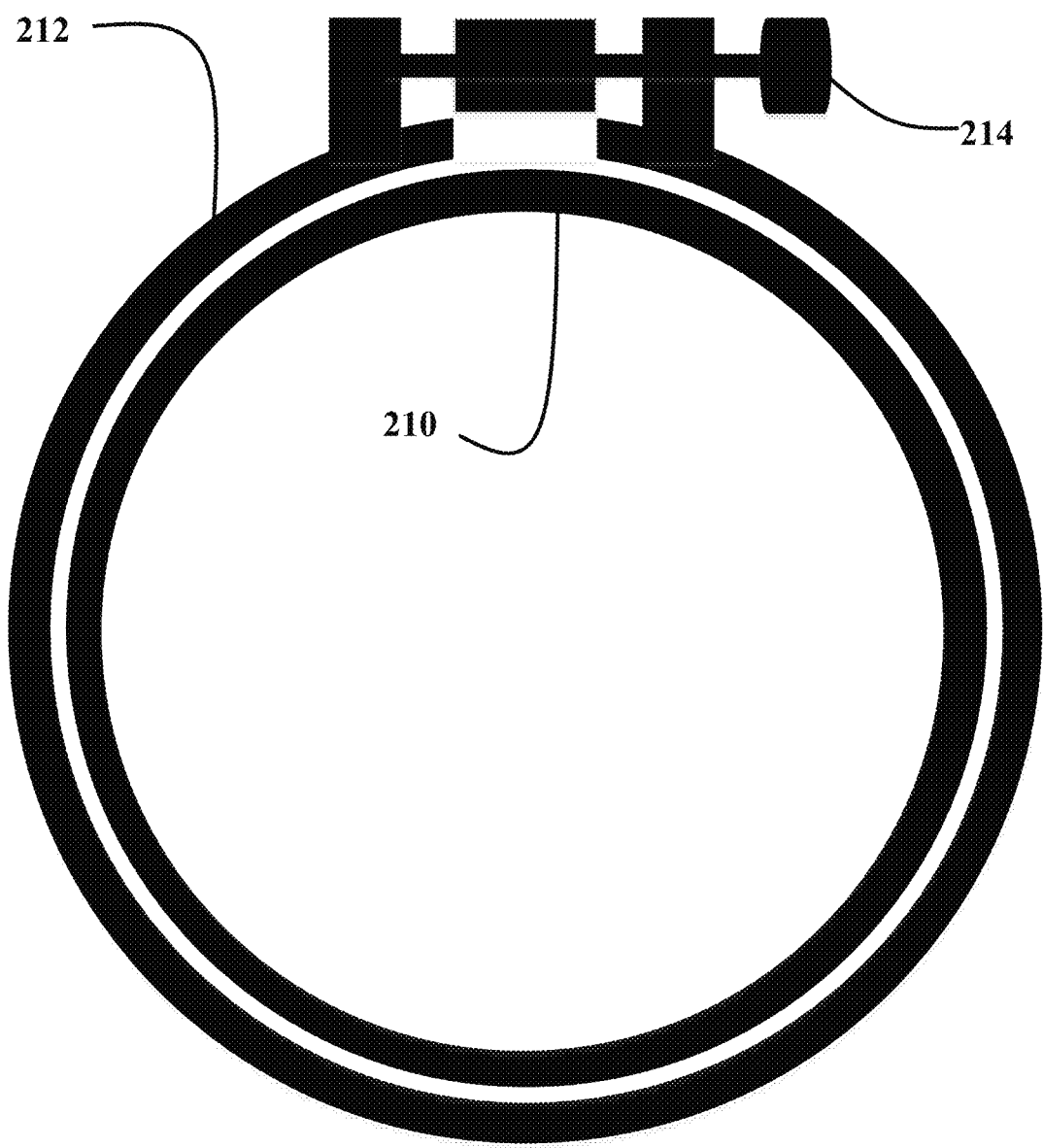
FIG. 2B illustrate a schematic view of a second exemplary structure of an exemplary holder for fixing a fabric, consistent with one or more exemplary embodiments of the present disclosure.

FIG. 2B illustrates a schematic view of a second exemplary structure of a holder 208 configured to fix fabric 112 thereon, consistent with one or more exemplary embodiments of the present disclosure. In an exemplary embodiment, holder 208 may be placed and firmed around fabric 112. As used herein, firmed may refer to holder 208 being fixed or fastened around fabric 112. In an exemplary embodiment, holder 208 may include a hoop 210 and a frame 212 configured to fix fabric 112. In an exemplary embodiment, to fix fabric 112 utilizing holder 208, fabric 112 may be spread on hoop 210 and then frame 212 may be placed on fabric 112. In an exemplary embodiment, frame 212 may include a tightening device 214 configured to fasten frame 212 around hoop 210. In an exemplary embodiment, tightening device 214 may include a screw, for example, a metal screw.

Figure 1B:
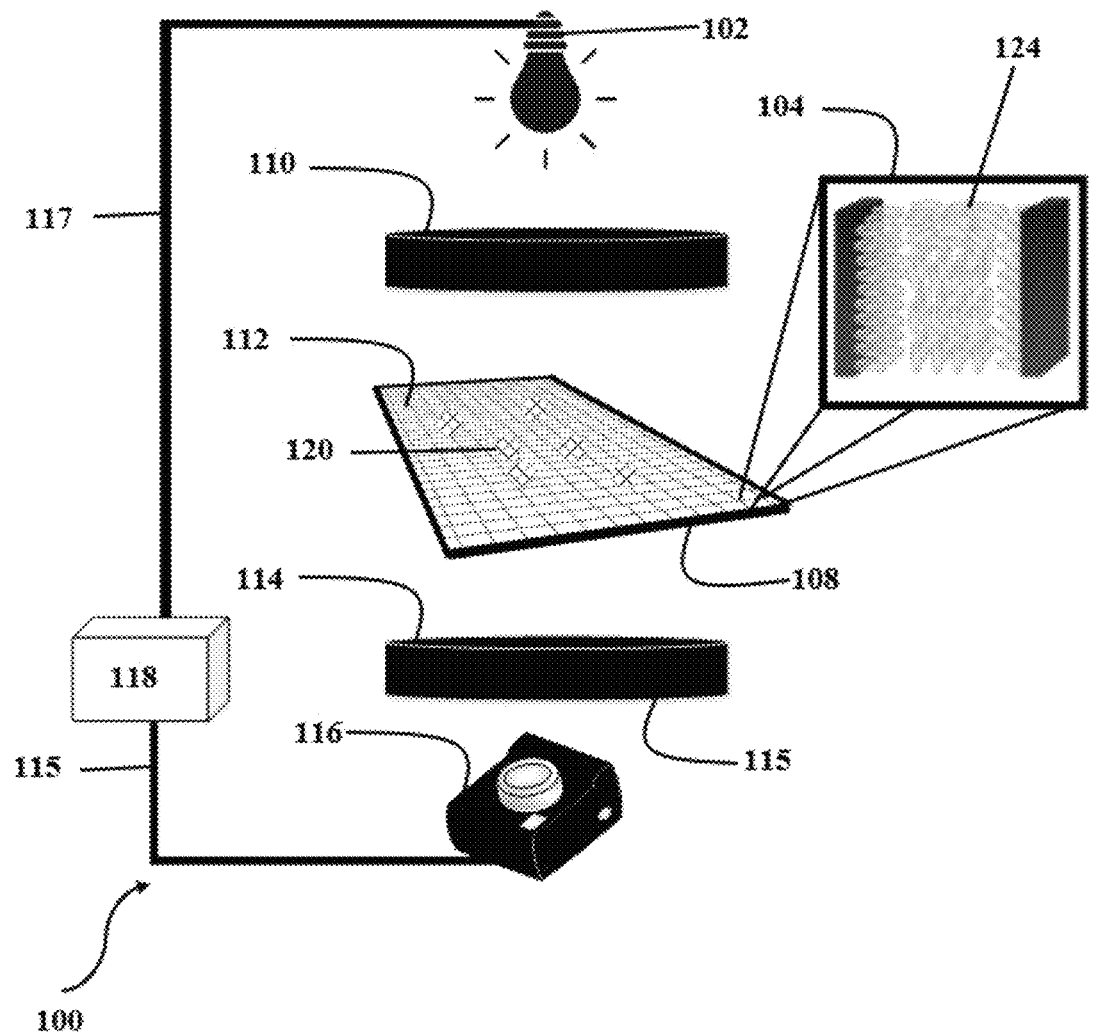
FIG. 1B illustrates a schematic view of an exemplary system for detecting a target material in an exemplary sample after adding the sample to the system, consistent with one or more exemplary embodiments of the present disclosure.

FIG. 1B illustrates a schematic view of system 100 for detecting a target material in a sample after adding sample 120 to system 100, consistent with one or more exemplary embodiments of the present disclosure. In an exemplary embodiment as may be seen in FIG. 1B, LCs 124 may reorient while being in contact with a target material in sample 120 in comparison with orientation of LCs 106 in FIG. 1A while being only in contact with air surrounding sensor 101. In an exemplary embodiment, an exemplary target material may include a biological or chemical species. In an exemplary embodiment, an exemplary target material may include a biological molecule, a gas, a molecule hovering in the air, a molecule dispersing in liquid, an alcohol, a molecule dissolved in a liquid, and combinations thereof. In an exemplary embodiment, an exemplary gas may include at least one of carbon monoxide, nitrogen, argon, carbon dioxide, and combinations thereof. In an exemplary embodiment, an exemplary biological molecule may include at least one of a polysaccharide, a lipid, a nucleic acid, an antibody, a protein, a carbohydrate, a virus, an antigen, a pathogen, a DNA, a RNA, and combinations thereof.

In an exemplary embodiment, an exemplary biological molecule may include at least one of herpes virus, influenza A, influenza B, and coronavirus, for example, COVID-19. In an exemplary embodiment, sample 120 may include a tissue or a fluid from a human, animal, or plant. In an exemplary embodiment, sample 120 may be at least one of saliva, mucus, blood, blood plasma, and urine. In an exemplary embodiment, an exemplary target material may include a contamination in sample 120 to be identified and/or quantified. In an exemplary embodiment, an exemplary target material may include methanol contamination in alcoholic drinks.

In an exemplary embodiment, system 100 may be utilized for diagnosing a subject as having a disorder, in which a presence of a target biological molecule in a sample 120 may indicate a presence of the disorder. In an exemplary embodiment, an exemplary disorder may be an infectious disease. Additionally, an exemplary disease may be dengue fever, AIDS, hepatitis, sexually transmitted diseases, antibiotic resistance, and the like. Furthermore, in an exemplary embodiment, system 100 disclosed here may be utilized for detecting at least one of vibration, acceleration, and flow of molecules. In an exemplary embodiment, system 100 disclosed here may be utilized for detecting at least one of temperature, pH, ions such as $H^+$, concentration of ions or molecules, and combinations thereof.

In an exemplary embodiment, adding an exemplary target material may change homeotropic orientation of LCs 106 in an exemplary pixel 104 and form LCs 124 due to an interaction between LCs 106 and exemplary target material.

In an exemplary embodiment, LCs 124 may have a specific pattern of orientations for each respective target material.

In an exemplary embodiment, a binding agent may be added to each respective pixel 104 of an exemplary array of pixels of fabric 112 allowing for enhancing interaction of exemplary sample 120 in gas phase with LCs 124. In an exemplary embodiment, the binding agent may absorb an exemplary target material in exemplary sample 120 so that leading to an enhanced interaction between an exemplary target material and LCs 124. In an exemplary embodiment, to detect and/or quantify gases, a binding agent may be added to fabric 112 and/or sample 120. In an exemplary embodiment, an exemplary binding agent may include at least one of diethanolamine, hexavalent vaccine (may contain antigen for diphtheria, tetanus, pertussis, poliomyelitis, haemophilus B, and hepatitis B), pantavalent vaccine (may contain antigen for diphtheria, pertussis, tetanus, hepatitis B and hemophilus influenza type B), aptamers (single-stranded DNA or RNA), and combinations thereof. In an exemplary embodiment, to analyze exemplary gases, 0.2 µL of diethanolamine may be added on fabric 112 utilizing a micropipette. In an exemplary embodiment, diethanolamine may be spread on fabric 112 using a disposable tip of an exemplary micropipette. In an exemplary embodiment, after 5 minutes, fabric 112 may be monitored under a microscope. In an exemplary embodiment, after 5 minutes exemplary square pixels may be empty and diethanolamine may be stuck to wrap and weft of fabric 112. In an exemplary embodiment, fabric 112 may be impregnated with LCs to monitor changes of gases velocity, concentration, etc. In an exemplary embodiment, exemplary binding agents may interact with exemplary target materials by physical and chemical interactions. In an exemplary embodiment, diethanolamine may interact with carbon dioxide by chemical bindings that may produce a positive hydrogen atom.

In an exemplary embodiment, when sample 120 is in a liquid phase, a volume in a range of 0.1 µL to 1 µL of sample 120 may be added on fabric 112 impregnated with LCs 124 utilizing a micropipette. In an exemplary embodiment, fabric 112 may be impregnated with a volume in a range of 0.0001 µL to 0.003 µL of sample 120 into each pixel of an exemplary array of pixels of fabric 112. In an exemplary embodiment, LCs 124 may change their orientation in contact with sample 120 containing an exemplary target material. In an exemplary embodiment, an exemplary light transmitted from light source 102 may path through sensor 101 containing LCs 124 with specific orientations due to an exemplary target material. In an exemplary embodiment, an exemplary light may refract due to orientations of LCs 124 in contact with an exemplary target material. In an exemplary embodiment, an exemplary refraction may induce a specific pattern for each target material. In an exemplary embodiment, image-capturing device 116 may take an image picture of a surface 115 of second polarizer 114. An exemplary image may contain a pattern formed by LCs 124. In an exemplary embodiment, exemplary images captured by image-capturing device 116 may be used to detect and/or quantify exemplary target materials in sample 120.

In an exemplary embodiment, a human and/or processing unit 118 may be used to detect and/or quantify exemplary target materials in sample 120. In an exemplary embodiment, processing unit 118 may include a memory and a processor to analyze exemplary pictures may be captured by image-capturing device 116. In an exemplary embodiment, an exemplary memory may contain processor-readable instructions to give instructions to an exemplary processor. In an exemplary embodiment, processing unit 118 may be electrically connected to image-capturing device 116 utilizing electrical line 115 and processing unit 118 may be electrically connected to light source 102 utilizing electrical line 117. In an exemplary embodiment, processing unit 118 may be connected to light source 102 and image-capturing device 116 using electrical wireless connections. In an exemplary embodiment, processing unit 118 may be configured to transmit light utilizing light source 102. In an exemplary embodiment, processing unit 118 may be additionally configured to take pictures of a surface of second polarizer 114 utilizing image-capturing device 116. In an exemplary embodiment, processing unit 118 may be further configured to detect and/or quantify an exemplary target material in sample 120. In an exemplary embodiment, each respective picture may include a pattern formed by orientations of LCs 124. In an exemplary embodiment, processing unit 118 may be a computer system illustrated in FIG. 3 herein below, that may use machine learning techniques for image processing of an exemplary pattern of an image taken from surface of second polarizer 114. In an exemplary embodiment, processing unit 118 may be configured to analyze exemplary pictures captured by image-capturing device 116 for detection and/or quantification of exemplary target materials in sample 120. An exemplary method of detection and/or quantification may be illustrated in step 410 of flowchart 400 herein below.

Figure 3:
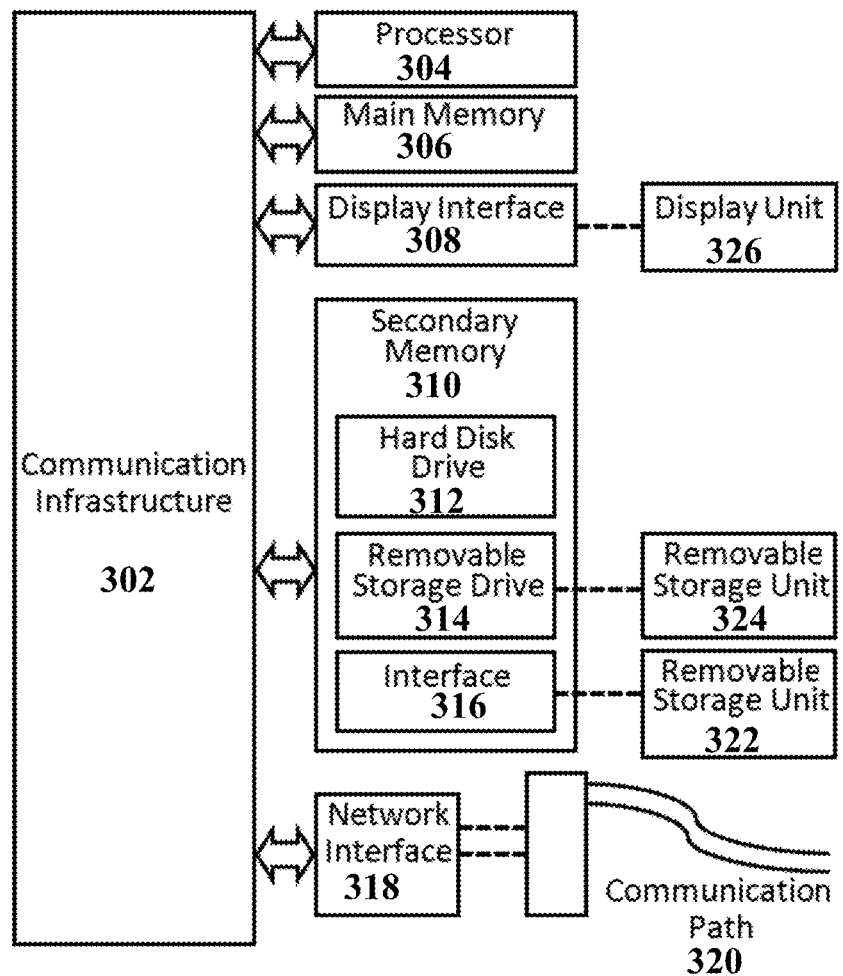
FIG. 3 illustrates a computer system in which an embodiment of the present disclosure, or portions thereof, may be implemented as computer-readable code, consistent with one or more exemplary embodiments of the present disclosure.

In an exemplary embodiment, processing unit 118 may include a computer system. FIG. 3 illustrates a computer system 300 in which an embodiment of the present disclosure, or portions thereof, may be implemented as computer-readable code, consistent with one or more exemplary embodiments of the present disclosure. For example, step 410 of flowchart 400 may be implemented in computer system 300 using hardware, software, firmware, tangible computer readable media having instructions stored thereon, or a combination thereof and may be implemented in one or more computer systems or other processing systems. Hardware, software, or any combination of such may embody any of the modules and components in FIG. 1A and FIG. 1B. In an exemplary embodiment, computer system 300 may include processor 304.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multiprocessor machines. In addition, in some embodiments the order of operations may be rearranged without departing from the spirit of the disclosed subject matter.

Processor 304 may be a special purpose or a general-purpose processor device. As will be appreciated by persons skilled in the relevant art, processor 304 may also be a single processor in a multi-core/multiprocessor system, such system operating alone, or in a cluster of computing devices operating in a cluster or server farm. Processor 304 may be connected to a communication infrastructure 302, for example, a bus, message queue, network, or multi-core message-passing scheme.

In an exemplary embodiment, computer system 300 may include a display interface 308, for example a video connector, to transfer data to a display unit 326, for example, a monitor. Computer system 300 may also include a main memory 306, for example, random access memory (RAM), and may also include a secondary memory 310. Secondary memory 310 may include, for example, a hard disk drive 312, and a removable storage drive 314. Removable storage drive 314 may include a floppy disk drive, a magnetic tape drive, an optical disk drive, a flash memory, or the like. Removable storage drive 314 may read from and/or write to a removable storage unit 324 in a well-known manner. Removable storage unit 324 may include a floppy disk, a magnetic tape, an optical disk, etc., which may be read by and written to by removable storage drive 314. As will be appreciated by persons skilled in the relevant art, removable storage unit 324 may include a computer usable storage medium having stored therein computer software and/or data.

In alternative implementations, secondary memory 310 may include other similar means for allowing computer programs or other instructions to be loaded into computer system 300. Such means may include, for example, a removable storage unit 322 and an interface 316. Examples of such means may include a program cartridge and cartridge interface (such as that found in video game devices), a removable memory chip (such as an EPROM, or PROM) and associated socket, and other removable storage units 322 and interfaces 316 which allow software and data to be transferred from removable storage unit 322 to computer system 300.

Computer system 300 may also include a network interface 318. Network interface 318 allows software and data to be transferred between computer system 300 and external devices. Network interface 318 may include a modem, a network interface (such as an Ethernet card), a communications port, a PCMCIA slot and card, or the like. Software and data transferred via network interface 318 may be in the form of signals, which may be electronic, electromagnetic, optical, or other signals capable of being received by network interface 318. These signals may be provided to network interface 318 via a communications path 320. Communications path 320 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 324, removable storage unit 322, and a hard disk installed in hard disk drive 312. Computer program medium and computer usable medium may also refer to memories, such as main memory 306 and secondary memory 310, which may be memory semiconductors (e.g. DRAMs, etc.).

Computer programs (also called computer control logic) are stored in main memory 306 and/or secondary memory 310. Computer programs may also be received via network interface 318. Such computer programs, when executed, enable computer system 300 to implement different embodiments of the present disclosure as discussed herein. In particular, the computer programs, when executed, enable processor device 304 to implement the processes of the present disclosure, such as the operations in method 400 illustrated by flowchart 400 of FIG. 4, discussed below. Accordingly, such computer programs represent controllers of computer system 300. Where an exemplary embodiment of method 400 is implemented using software, the software may be stored in a computer program product and loaded into computer system 300 using removable storage drive 314, interface 316, and hard disk drive 312, or network interface 318.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks. CD ROMS, ZIP disks, tapes, magnetic storage devices, and optical storage devices, MEMS, nano-technological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed. In an exemplary implementation, exemplary system 100 may be configured to detect a target material in a sample via analyzing patterns formed by LCs in contact with the target material. Exemplary system 100 may be utilized by a method 400 for detection and/or quantification of target materials described herein below. In an exemplary embodiment, processing unit 118 may include a computer system similar to computer system 300.

Figure 4:
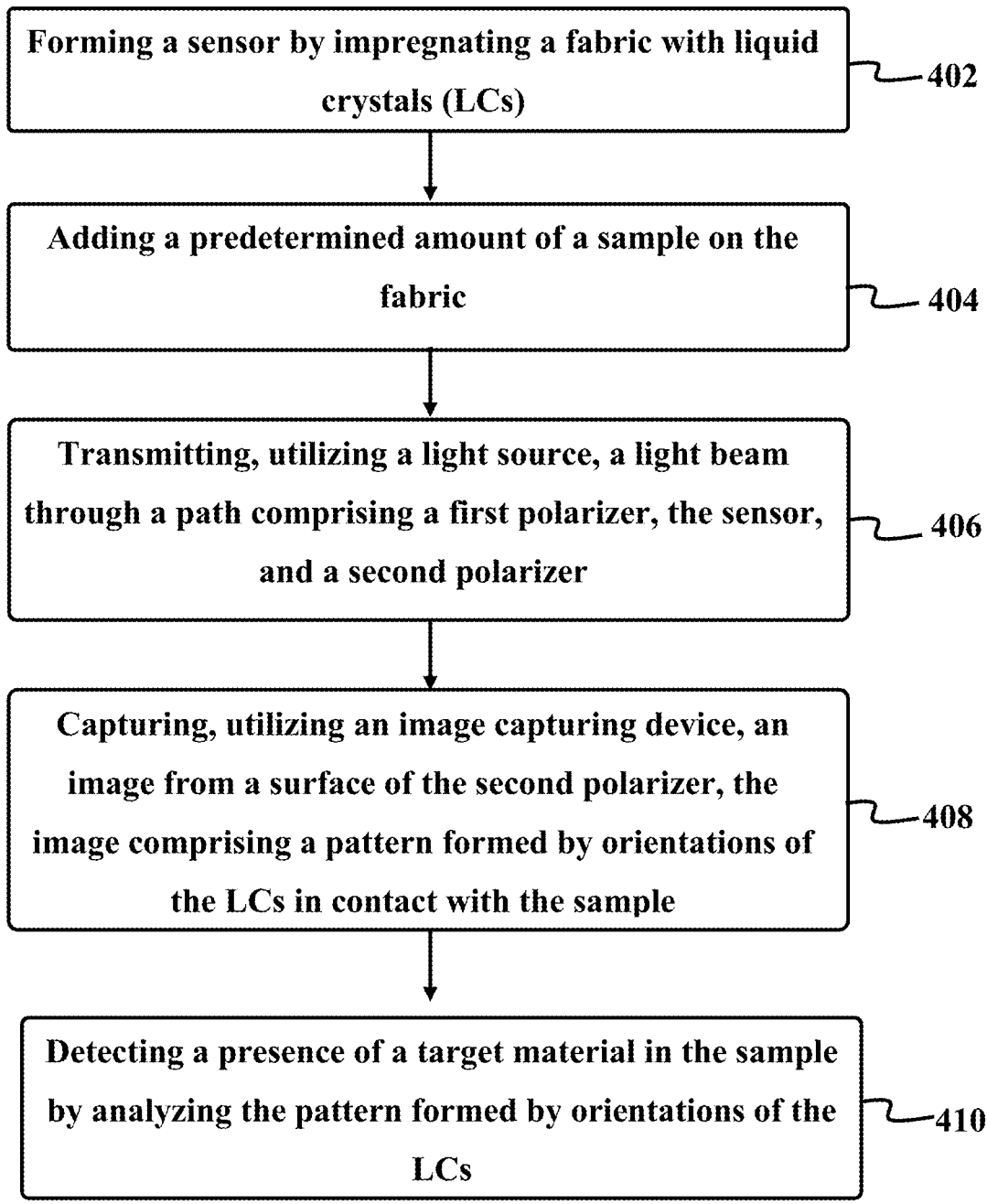
FIG. 4 illustrates a flowchart of an exemplary method for detecting a target material in a sample, consistent with one or more exemplary embodiments of the present disclosure.

According to one or more exemplary embodiments, the present disclosure is further directed to exemplary embodiments of a method for detecting and/or quantifying a target material in a sample. In an exemplary embodiment, a concentration or amount of a target material may be detected utilizing exemplary method. FIG. 4 illustrates a flowchart of exemplary method 400 to detect a target material in a sample, consistent with one or more exemplary embodiments of the present disclosure. In an exemplary embodiment, method 400 may include a step 402 of forming a sensor by impregnating a fabric with liquid crystals (LCs), a step 404 of adding a predetermined amount of a sample on the fabric, a step 406 of transmitting, utilizing a light source, a light beam through a path comprising a first polarizer, the sensor, and a second polarizer, a step 408 of capturing, utilizing an image-capturing device, an image from a surface of the second polarizer, the image comprising a pattern formed by orientations of the LCs in contact with the sample, and a step 410 of detecting a presence of a target material in the sample by analyzing the pattern formed by orientations of the LCs. In an exemplary implementation, method 400 may be conducted and perform utilizing exemplary system 100 described herein above.

In an exemplary embodiment, step 402 of forming a sensor may include forming exemplary sensor 101 by impregnating fabric 112 with liquid crystals (LCs) 106 with a volume of LCs in a range of 0.01 μL to 0.1 μL. In an exemplary embodiment, fabric 112 may be impregnated with LCs 106 at a volume in a range of 0.0001 μL to 0.0005 μL into each pixel 104 of an exemplary array of pixels of fabric 112. In an exemplary embodiment, to impregnate fabric 112 with LCs 106, a micropipette may be used to add LCs 106 inside an exemplary array of pixels of fabric 112. In an exemplary embodiment, an exemplary micropipette may be a device with disposable tip for aspirating liquids. In an exemplary embodiment, after adding LCs 106 utilizing an exemplary micropipette, a disposable tip may be used to spread LCs 106 on fabric 112. In an exemplary embodiment, an exemplary disposable tip may be sterile. In an exemplary embodiment, as used herein pixel may refer to a square hole formed by warp and weft of fabric 112. In an exemplary embodiment each respective pixel 104 of an exemplary array of pixels may include a dimension in a range of 1 μm to 600 μm. In an exemplary embodiment, fabric 112 may include a thickness in a range of 10 μm to 100 μm. In an exemplary embodiment, fabric 112 may be made of at least one of polyester, rayon, linen, nylon, silk, and combinations thereof. In an exemplary embodiment, LCs 106 may include at least one of thermotropic LCs, lyotropic LCs, and combinations thereof. In an exemplary embodiment, an exemplary thermotropic LCs may include at least one of nematic LCs, smectic LCs, chiral phases, twisted nematic LCs, discotic LCs, conic LCs, and combinations thereof. LCs 106 may be homeotropically aligned when air may be in contact with LCs 106 from top and bottom of sensor 101.

In an exemplary embodiment, step 402 of forming the sensor may further include adding a binding agent to each respective pixel 104 of an exemplary array of pixels of fabric 112 allowing for enhancing interaction of exemplary sample 120 in gas phase with LCs 124. In an exemplary embodiment, to detect and/or quantify gases, a binding agent may be added to fabric 112 and/or sample 120. In an exemplary embodiment, an exemplary binding agent may include at least one of diethanolamine, hexavalent vaccine (may contain antigen for diphtheria, tetanus, pertussis, poliomyelitis, haemophilus B, and hepatitis B), pantavalent vaccine (may contain antigen for diphtheria, pertussis, tetanus, hepatitis B and hemophilus influenza type B), aptamers (single-stranded DNA or RNA), and combinations thereof. In an exemplary embodiment, to analyze exemplary gases, 0.2 μL of diethanolamine may be added on fabric 112 utilizing a micropipette. In an exemplary embodiment, diethanolamine may be spread on fabric 112 using a disposable tip of an exemplary micropipette. In an exemplary embodiment, after 5 minutes, fabric 112 may be monitored under a microscope. In an exemplary embodiment, after 5 minutes exemplary square pixels may be empty and diethanolamine may be stuck to wrap and weft of fabric 112. In an exemplary embodiment, fabric 112 may be impregnated with LCs to monitor changes of gases velocity, concentration, etc. In an exemplary embodiment, exemplary binding agents may interact with exemplary target materials by physical and chemical interactions. In an exemplary embodiment, diethanolamine may interact with carbon dioxide by chemical bindings that may produce a positive hydrogen atom.

In an exemplary embodiment, sensor 101 may include fabric 112 and LCs 106. In an exemplary embodiment, sensor 101 may further include holder 108 placed around fabric 112. In an exemplary embodiment, holder 108 may be used to eliminate elasticity of fabric 112 by fixing fabric 112 in a planar surface. In an exemplary embodiment, holder 108 may include holder 204 or holder 208. In an exemplary embodiment, holder 204 may include plate 207 with a plurality of open-ended holes 206 on plate 207 with a clamp and/or an adhesive substance to fasten fabric 112 on an exemplary plate. In an exemplary embodiment, holder 208 may include hoop 210 and frame 212 to fix fabric 112. In an exemplary embodiment, holder 208 may include a pair of concentric circular or elliptical rings (hoop 210 and frame 212) in which a larger ring (frame 212) may include a tightening device 214, in a form of a metal screw to fix hoop 210 and frame 212 together.

In an exemplary embodiment, step 404 of adding a predetermined amount of a sample on fabric 112 may include adding sample 120 at a volume in a range of 0.1 μL to 1 μL on fabric 112. In an exemplary embodiment, sample 120 may be added on fabric 112 at a volume in a range of 0.0001 μL to 0.003 μL of sample 120 into each pixel 106 of an exemplary array of pixels of fabric 112. In an exemplary embodiment, sample 120 may be added on fabric 112 utilizing a micropipette if sample 120 is a liquid and/or a dispersed material in a liquid. In an exemplary embodiment, when sample 120 is a gas, a predetermined volume of an exemplary gas may be purged inside a chamber where sensor 101 may be placed therein. In an exemplary embodiment, an exemplary chamber may include an inlet and an outlet for an exemplary gas. In an exemplary embodiment, an exemplary gas may be purged inside an exemplary chamber to be detected and/or quantified by analyzing images captured utilizing image-capturing device 116. In an exemplary embodiment, exemplary images may contain patterns formed by orientations of LCs being in contact with sample 120. In an exemplary embodiment, an exemplary gas may include at least one of carbon monoxide, nitrogen, argon, carbon dioxide, and combinations thereof. In an exemplary embodiment, an exemplary target material may include a biological or chemical species. In an exemplary embodiment, an exemplary target material may include at least one of a gas molecule, a liquid molecule, and combinations thereof. In an exemplary embodiment, an exemplary target material may include a biological molecule, a gas, a molecule hovering in the air, a molecule dispersing in liquid, an alcohol, a molecule dissolved in a liquid, and combinations thereof. In an exemplary embodiment, an exemplary biological molecule may include at least one of a polysaccharide, a lipid, a nucleic acid, an antibody, a protein, a carbohydrate, a virus, an antigen, a pathogen, a DNA, a RNA, and combinations thereof.

In an exemplary embodiment, an exemplary biological molecule may include at least one of herpes virus, influenza A, influenza B, and coronavirus, for example, COVID-19. In an exemplary embodiment, sample 120 may include a tissue or a fluid from a human, animal, or plant. In an exemplary embodiment, sample 120 may be at least one of saliva, mucus, blood, blood plasma, and urine. In an exemplary embodiment, an exemplary target material may include a contamination in a sample to be identified and/or quantified. In an exemplary embodiment, an exemplary target material may include methanol contamination in alcoholic drinks.

In an exemplary embodiment, method 400 may be used for diagnosing a subject having a disorder, wherein a presence of a target biological molecule in the sample may indicate a presence of the disorder. In an exemplary embodiment, the disorder may be an infectious disease. Additionally, an exemplary disease may be Dengue fever, AIDS, hepatitis, sexually transmitted diseases, antibiotic resistance, and the like. Furthermore, in an exemplary embodiment, method 400 disclosed here may be utilized for detecting at least one of vibration, acceleration, and flow of molecules. In an exemplary embodiment, method 400 disclosed here may be used for detecting at least one of temperature, pH, ions such as $H^+$, concentration of ions or molecules, and combinations thereof.

In an exemplary embodiment, LCs 106 may reorient when being in contact with sample 120 containing an exemplary target material. In an exemplary embodiment, LCs 106 with homeotropic orientation may change to LCs 124 with a new orientation which may be specific for each target material. In an exemplary embodiment, specific orientation of LCs 124 may form a specific pattern observable in an exemplary image captured from a surface of second polarizer 114. In an exemplary embodiment, an exemplary specific pattern may be used to detect and/or quantify an exemplary target material in sample 120.

In an exemplary embodiment, detecting an exemplary target material may include placing first polarizer 110 between light source 102 and sensor 101. In an exemplary embodiment, first polarizer 110 may be a linear polarizer. As used herein, an exemplary linear polarizer may refer to a polarizer that produces a beam of light from an unpolarized light beam, in which an electric vector of the produced beam of light in UV-Visible wavelength range is vibrating primarily in one direction. In an exemplary embodiment, an unpolarized light may be produced by light source 102. In an exemplary embodiment, light source 102 may include at least one of a LED lamp, an incandescent light bulb, a cellphone light, and combinations thereof. In an exemplary embodiment, first polarizer 110 may be placed at a distance less than 15 cm from sensor 101.

In an exemplary embodiment, detecting an exemplary target material may further include placing second polarizer 114 between image-capturing device 116 and sensor 101. In an exemplary embodiment, second polarizer 114 may be a linear polarizer that may produce linear polarized light. In an exemplary embodiment, as used herein, linear polarized light may refer to a polarized light with one transition direction produced from unpolarized light. In an exemplary embodiment, first polarizer 110 and second polarizer 114 may be a pair of crossed polarizers. As used herein, crossed polarizers are two polarizers in which a transmitted light beam of a first polarizer may have 90 degree difference with a transmitted light beam of a second polarizer. For example, when an unpolarized light beam from light source 102 may be transmitted in a path through first polarizer 110, a beam of polarized light with a zero angle may be emitted from first polarizer 110. In an exemplary embodiment, after emitting light with one direction from first polarizer 110, light beam may pass through sensor 101 which may contain LCs 106 with homeotropic alignment. In an exemplary embodiment, light beam may pass through LCs 106 with no light refraction. In an exemplary embodiment, an exemplary light beam may pass through first polarizer 110, sensor 101, and may reach second polarizer 114. In an exemplary embodiment, light beam with 90 degree difference from a transmitted light from first polarizer 110 may have a permission to exit from second polarizer 114. In an exemplary embodiment, due to 90 degree difference of transmitted light beam angle, no light, may exit from second polarizer 114 and image-capturing device 116 may take a dark photo of surface 115 of second polarizer 114. In an exemplary embodiment, sample 120 which may contain a target material may be added on LCs 124. In an exemplary embodiment, LCs 124 may reorient in contact with exemplary target materials. In an exemplary embodiment, reorientation of LCs 124 may induce light refraction and therefore, light beams may exit from second polarizer 114. Therefore, a pattern may be produced with transmitted light from second polarizer 114 and an exemplary pattern may be captured utilizing image-capturing device 116. In an exemplary embodiment, an exemplary pattern may be specific for every target material. In an exemplary embodiment, second polarizer 114 may be placed at a distance in a range of 0.2 cm to 30 cm to sensor 101.

In an exemplary embodiment, step 406 of transmitting a light beam may be done by processing unit 118 utilizing light source 102. In an exemplary embodiment, an exemplary light beam may be produced utilizing light source 102. In an exemplary embodiment, processing unit 118 may be electrically connected to light source 102 utilizing electrical line 117. In another exemplary embodiment, light source 102 may work utilizing wireless electrical connections and may be controlled manually by pushing a button. In an exemplary embodiment, an exemplary produced light beam utilizing light source 102 may transmit through a pass from first polarizer 110, sensor 101, and second polarizer 114, respectively. In an exemplary embodiment, a full unpolarized light in UV-Visible wavelength range may be produced utilizing light source 102. In an exemplary embodiment, light source 102 may include at least one of a LED lamp, an incandescent light bulb, a cellphone light, and combinations thereof.

In an exemplary embodiment, step 408 of capturing an image from a surface of second polarizer 114 may include capturing an exemplary picture utilizing image-capturing device 116. In an exemplary embodiment, an exemplary image may include a pattern formed by orientations of LCs 124. In an exemplary embodiment, an exemplary pattern may be used to detect and/or quantify exemplary target materials. In an exemplary embodiment, image-capturing device 116 may be electrically connected to processing unit 118 utilizing electrical line 115. In an exemplary embodiment, processing unit 118 may control image-capturing device 116 by giving instructions to image-capturing device 116 for taking pictures. In another exemplary embodiment, image-capturing device 116 may work utilizing wireless electrical connections and may be controlled manually by pushing a button.

In an exemplary embodiment, step 410 of detecting a presence of the target material in the sample may be performed utilizing processing unit 118 after a time period of 10 seconds to 10 minutes of adding sample 120 onto fabric 112. In an exemplary embodiment, capturing an image from a surface of second polarizer 114 may be performed after a time period of 10 seconds to 10 minutes of adding sample 120 onto fabric 112. In an exemplary embodiment, fabric 112 may be impregnated with sample 120 2 minutes after adding sample 120 onto fabric 112. In an exemplary embodiment, adding sample 120 onto fabric 112 may lead to an interaction between sample 120 and LCs 106; thereby, resulting in reorienting of LCs 106 and forming LCs 124.

In an exemplary embodiment, processing unit 118 may include a memory and a processor. In an exemplary embodiment, an exemplary memory may use processor-readable instructions to be used by an exemplary processor. In an exemplary embodiment, an exemplary processing unit may be a computer system similar to computer system 300 shown in FIG. 3. In an exemplary embodiment, an exemplary target material in sample 120 may be detected by human and/or a processing unit using a machine learning technique. In an exemplary embodiment, orientations of LCs 124 may form different patterns which may be analyzed by human for specifying positive and negative samples. In an exemplary embodiment, exemplary patterns may be compared with a set of reference patterns by human. In an exemplary embodiment, an exemplary set of reference patterns may be formed by analyzing sample 120 containing exemplary target materials and capturing images from a surface of second polarizer 114. In an exemplary embodiment, a presence of a target material may be detected in sample 120, when an exemplary pattern of sample 120 be the same as a reference pattern of an exemplary set of reference patterns.

In an exemplary embodiment, an exemplary target material in sample 120 may also be detected utilizing processing unit 118 using an exemplary machine learning technique. In an exemplary embodiment, an exemplary machine learning technique is a method that uses machine learning algorithms to use historical data as an input and accurately predicting an output. In an exemplary embodiment, exemplary data of an exemplary set of reference patterns that may contain exemplary target materials and negative set of reference patterns that may be free of exemplary target materials may be collected in an exemplary memory. In an exemplary embodiment, each reference pattern of an exemplary set of reference patterns may form an array of vectors. In an exemplary embodiment, produced data may be collected in an exemplary memory for further analysis by an exemplary processor. In an exemplary embodiment, LCs 124 may reorient in contact with exemplary target materials. In an exemplary embodiment, reorientations of LCs 124 may induce forming patterns with different colors. In an exemplary embodiment, exemplary vectors may be formed responsive to orientations of LCs 124. In an exemplary embodiment, each respective vector of an exemplary array of vectors may determine a direction which may correspond to an orientation of LCs 124 in a respective pixel of an exemplary array of pixels. In an exemplary embodiment, each respective pixel of an exemplary array of pixels may have a color spectrum corresponding to orientations of LCs 124. In an exemplary embodiment, processing unit 118 may use color spectrums of exemplary patterns to extract an exemplary array of vectors. In an exemplary embodiment, an exemplary machine learning technique may use an exemplary array of vectors to differentiate between exemplary target materials. In an exemplary embodiment, orientations of LCs 124 may form a specific pattern for each target material. In an exemplary embodiment, processor 118 may compare an exemplary array of vectors formed by orientations of LCs in sample 120 with an exemplary array of vectors formed by orientations of LCs in an exemplary set of reference patterns. In an exemplary embodiment, a presence of exemplary target materials may be detected when an exemplary array of vectors of a pattern formed by orientations of LCs 124 may have a similarity of more than 80% to an exemplary array of vectors of a reference pattern of an exemplary set of reference patterns. In an exemplary embodiment, there may be a similarity factor between an exemplary pattern of sample 120 and one of reference patterns. In an exemplary embodiment, an exemplary similarity factor may be more than a threshold percent. In an exemplary embodiment, an exemplary similarity factor may be more than 70%. In another exemplary embodiment, an exemplary similarity factor may be more than 80%. In an exemplary embodiment, to detect an exemplary target material in sample 120, at least 70% of exemplary pixels in the presence of sample 120 may have LCs with the same orientations to LCs of one of reference patterns. In an exemplary embodiment, orientations of LCs of at least 80% pixels of an exemplary array of pixels in the presence of sample 120 may be the same with orientations of LCs of the at least 80% pixels of exemplary array of pixels in the presence of a reference sample.

In an exemplary embodiment, an amount of an exemplary target material in sample 120 may be detected by an exemplary machine learning technique. In an exemplary embodiment, an exemplary processor may collect patterns from image-capturing device 116 and compare exemplary patterns with a set of reference patterns in an exemplary memory. In an exemplary embodiment, an exemplary set of reference patterns may be prepared from a set of reference samples wherein each respective reference sample of an exemplary set of reference samples may contain a predetermined concentration of a target material. In an exemplary embodiment, the machine learning technique and the image processing technique may be used to analyze exemplary images may be taken utilizing image-capturing device 116. In an exemplary embodiment, every pattern produced by orientations of LCs 124 may form an array of vectors. In an exemplary embodiment, each respective vector of an exemplary array of vectors may determine a direction which may be corresponding to an orientation of LCs 124 in a respective pixel of an exemplary array of pixels. In an exemplary embodiment, each respective pixel of an exemplary array of pixels may include a color spectrum corresponding to orientations of LCs 124. In an exemplary embodiment, processing unit 118 may use color spectrums of exemplary patterns to extract an exemplary array of vectors. In an exemplary embodiment, to detect an exemplary amount of exemplary target materials in sample 120, an exemplary array of vectors of sample 120 may be compared with an exemplary array of vectors of an exemplary set of reference patterns. In an exemplary embodiment, an exemplary set of reference patterns may correspond to a set of amounts of a target material. In an exemplary embodiment, an exemplary amount of an exemplary target material in sample 120 may be equal to a first amount of a target material of an exemplary plurality of target materials when an exemplary plurality of vectors for sample 120 may have a similarity of more than 80% to a first army of vectors of a reference pattern of an exemplary set of reference patterns.

In an exemplary embodiment, exemplary method 400 and exemplary system 100 may be utilized to detect COVID-19 infection in a person. In an exemplary embodiment, sample 120 may include at least one of a sputum sample, a blood sample, and a nasal mucosa sample acquired from a person who is suspected to be infected by COVID-19 virus. In an exemplary embodiment, step 410 of detecting a presence of the target material in the sample may include detecting a COVID-19 infection in sample 120 by analyzing the pattern formed by orientations of the LCs in the presence of sample 120.

Example 1: Preparing LCs-Based Sensors on a Fabric

Figure 5:
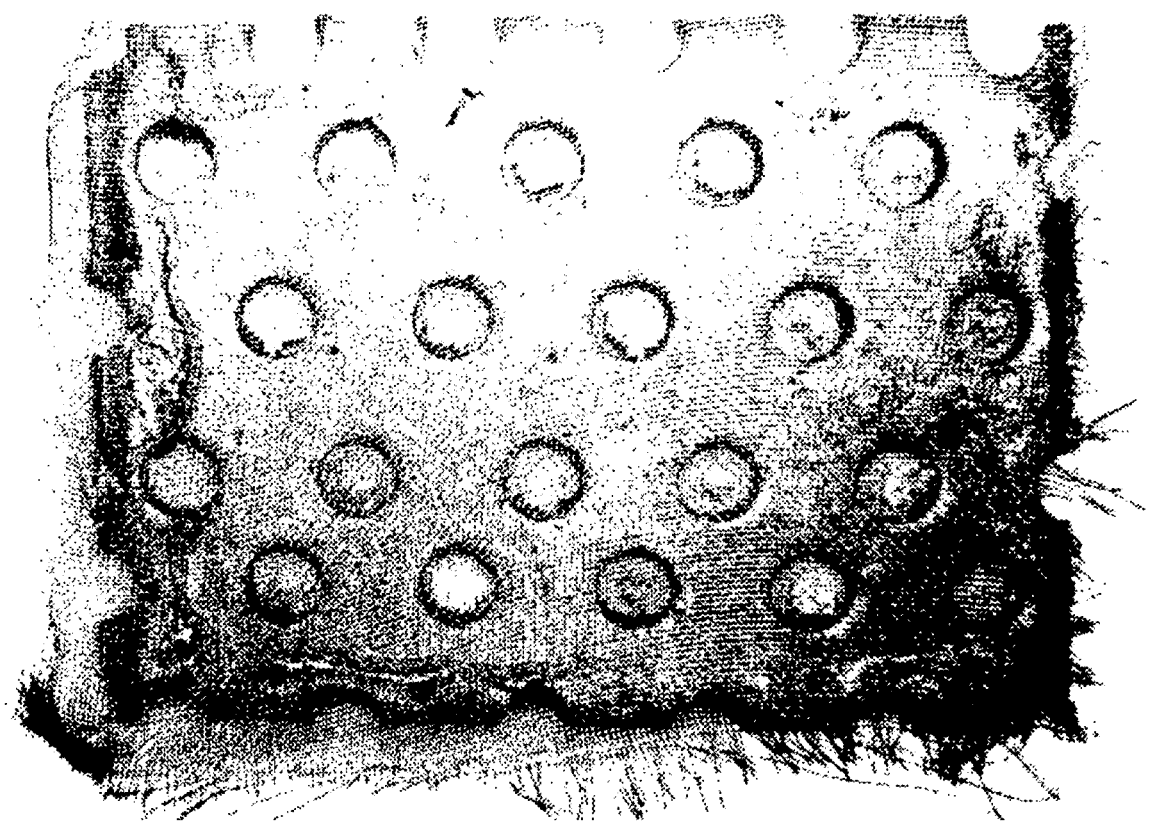
FIG. 5 illustrates an optical image of an exemplary sensor, consistent with one or more exemplary embodiments of the present disclosure.

In this example, an LCs-based sensor similar to sensor 101 was fabricated. To form an LCs-based sensor according to a method similar to method 400, a silk fabric was cleaned by placing the fabric in an autoclave under steam and pressure. A part of the fabric was impregnated with 0.02 µL of nematic E7. The nematic E7 LCs contained 51% 4-cyano-4'-pentylbiphenyl (5CB), 25% 4'-heptyl-4-biphenylcarbonitrile (7CB), 16% n-octyloxy-cyanobiphenyl (8O CB), and 8% 4-cyano-4'-pentylterphenyl 4-[4-(4-pentylphenyl)phenyl]benzonitrile (5CT). The LCs were aligned homeotropically due to a presence of air molecules in the top and the bottom of the LCs. The impregnated fabric with LCs was located between two polarizers in which the polarizers were placed on the top and on the bottom of the impregnated fabric. FIG. 5 illustrates an optical image of a sensor, consistent with one or more exemplary embodiments of the present disclosure. FIG. 5 shows a fabric fixed on a holder in which the fabric is fixed on the holder utilizing a glue. The fabric is impregnated with LCs to form a sensor.

Example 2: Detection Method of Influenza and COVID-19 Viruses

Figure 6A:
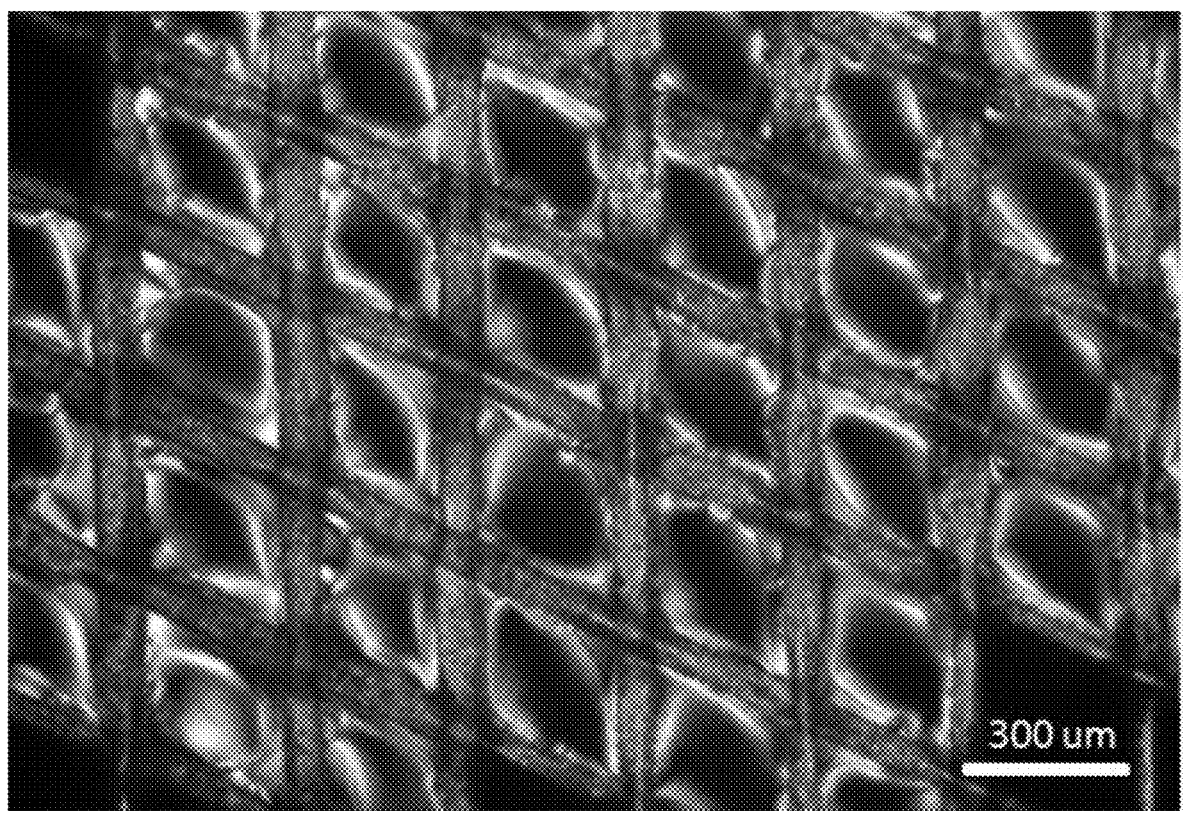
FIG. 6A illustrates a polarized image captured from a fabric impregnated with liquid crystals (LCs) placed between crossed polarizers utilizing a polarized light microscope, consistent with one or more exemplary embodiments of the present disclosure.
Figure 6B:
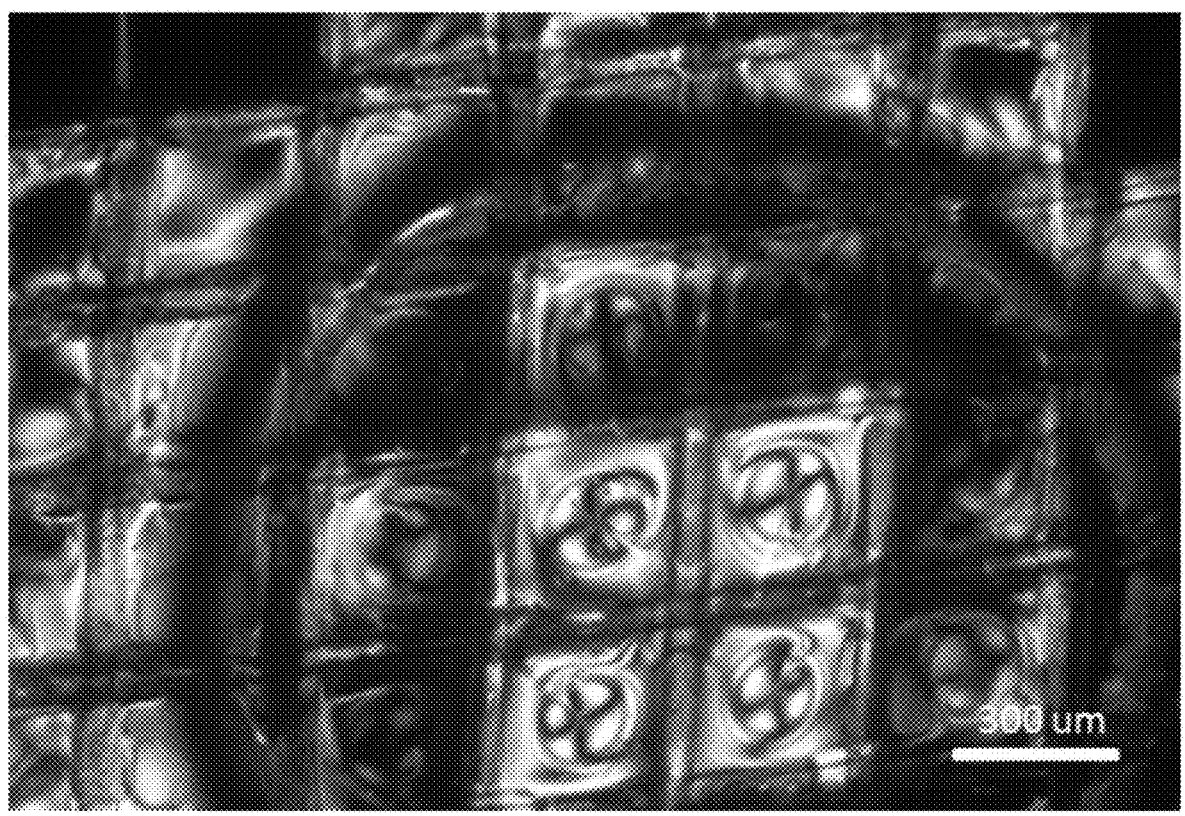
FIG. 6B illustrates a polarized image captured from influenza A viruses placed on an impregnated fabric with LCs utilizing a polarized light microscope, consistent with one or more exemplary embodiments of the present disclosure.
Figure 6C:
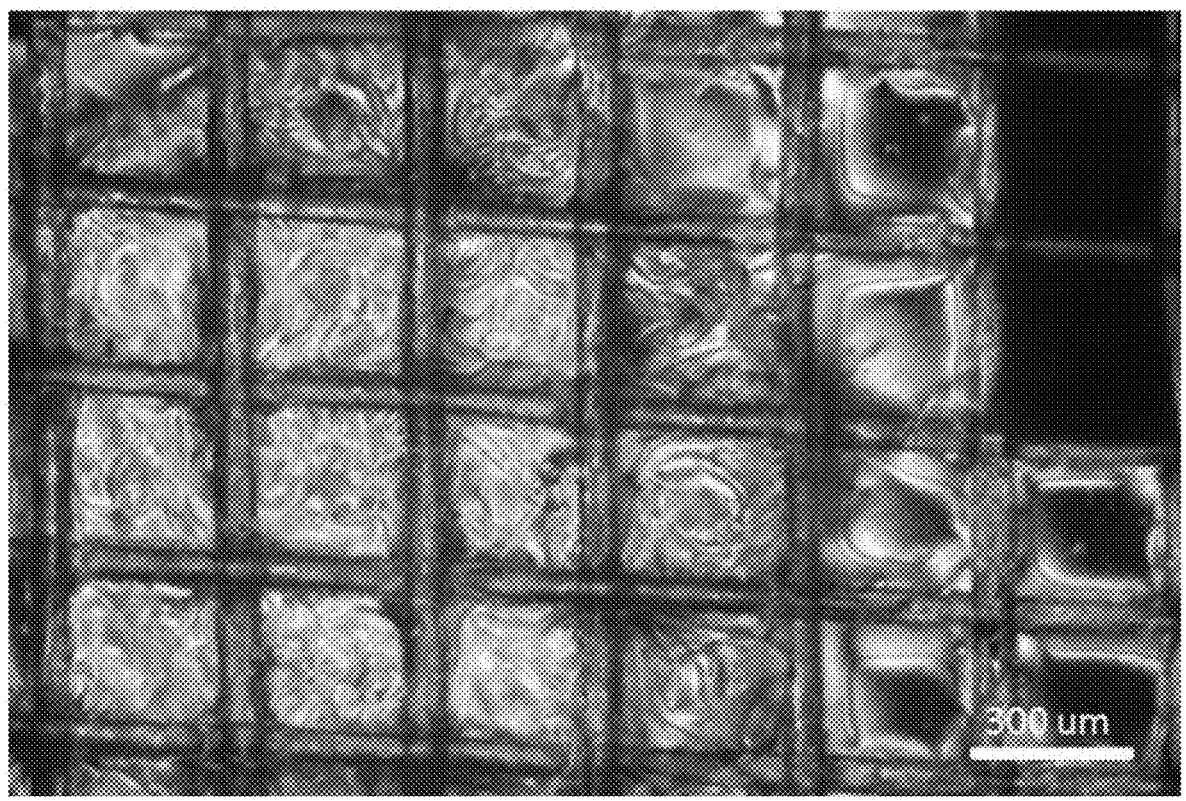
FIG. 6C illustrates a polarized image captured from influenza B viruses placed on an impregnated fabric with LCs utilizing a polarized light microscope, consistent with one or more exemplary embodiments of the present disclosure.
Figure 6D:
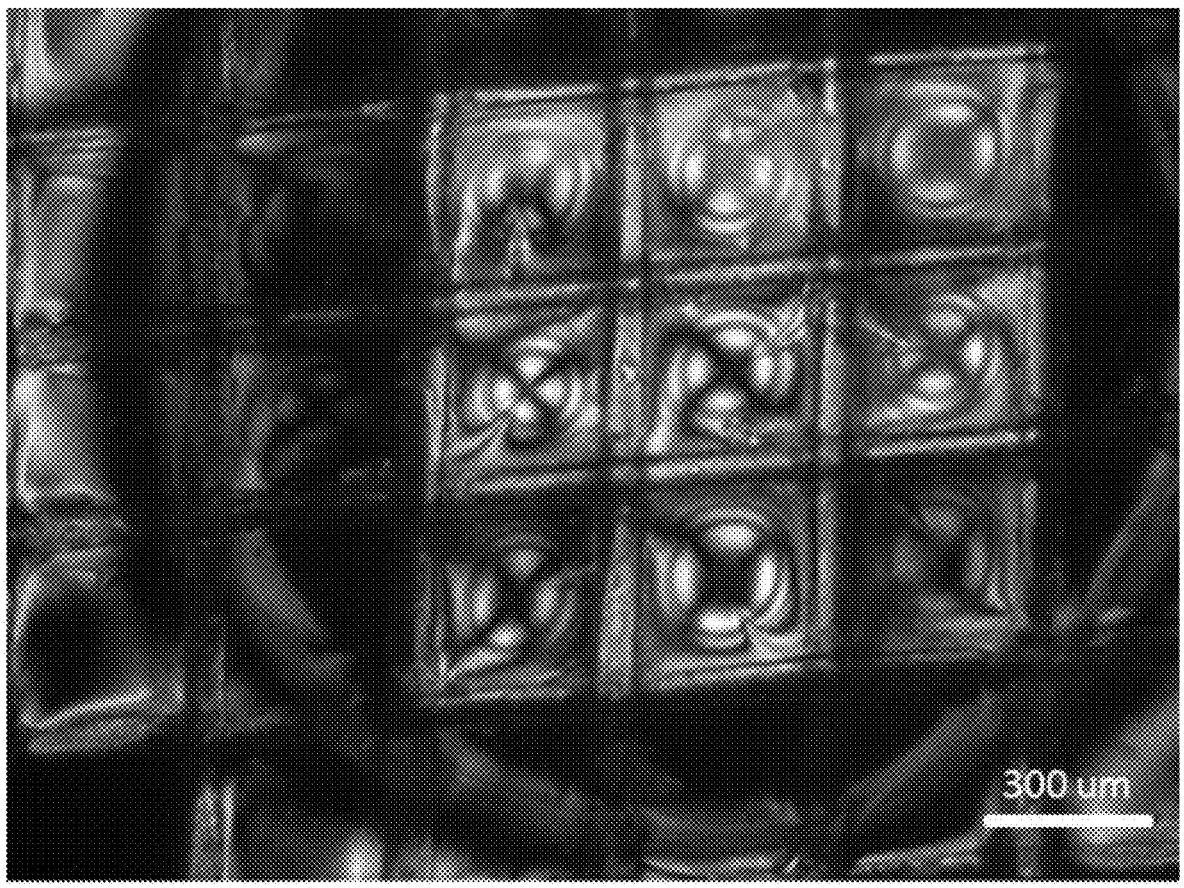
FIG. 6D illustrates a polarized image captured from COVID-19 viruses placed on an impregnated fabric with LCs utilizing a polarized light microscope, consistent with one or more exemplary embodiments of the present disclosure.

Detection of influenza A, influenza B, and COVID-19 viruses was performed using a method similar to method 400 and using a system similar to system 100. To detect influenza A, influenza B, and COVID-19 viruses, 0.1 μL of the sample of these viruses were replicated in a host cell. Then the samples were placed on LCs trapped in a fabric. After passing a light beam through a first polarizer similar to first polarizer 110, the light beam was refracted due to orientations of LCs in contact with samples of influenza A, influenza B, and COVID-19 viruses. The refracted light beam passed through a second polarizer similar to second polarizer 114 and a pattern was captured for each sample. A processor similar to processing unit 118 converted the pattern into vectors and compared the data with reference vectors. The processor identified influenza A, influenza B, and COVID-19 viruses due to a resemblance of the vectors of influenza A, influenza B, and COVID-19 viruses to the reference vectors of influenza A, influenza B, and COVID-19 viruses stored in the memory of the processor. The processor detected influenza A, influenza B, and COVID-19 viruses by measuring similarity of more than 80% between the vectors of the samples and the vectors of the reference samples. Exemplary reference samples were prepared based on various concentrations of influenza A, influenza B, and COVID-19 viruses. Therefore, concentrations of samples of influenza A, influenza B, and COVID-19 viruses can be measured according to the similarity factor of more than 80% between the vectors of the influenza A, influenza B, and COVID-19 samples and the vectors of the reference samples. FIG. 6A illustrates a polarized image captured from a fabric impregnated with liquid crystals (LCs) placed between crossed polarizers utilizing a polarized light microscope, consistent with one or more exemplary embodiments of the present disclosure. FIG. 6B illustrates a polarized image captured from influenza A viruses placed on an impregnated fabric with LCs utilizing a polarized light microscope, consistent with one or more exemplary embodiments of the present disclosure. Influenza A viruses were prepared in phosphate buffer solution (PBS) media before transferring to the impregnated fabric. FIG. 6C illustrates a polarized image captured from influenza B viruses placed on an impregnated fabric with LCs utilizing a polarized light microscope, consistent with one or more exemplary embodiments of the present disclosure. FIG. 6D illustrates a polarized image captured from COVID-19 viruses placed on an impregnated fabric with LCs utilizing a polarized light microscope, consistent with one or more exemplary embodiments of the present disclosure. Influenza B and COVID-19 viruses were prepared in PBS media before transferring to the impregnated fabric. As shown in FIGS. 6A to 6D, patterns of viruses in every polarized image were different which shows the capability of the sensor to differentiate between Influenza A. Influenza B, and COVID-19 viruses.

In an exemplary embodiment, a system similar to system 100 gives a precision of at least 94% for detecting COVID-19 viruses.

Example 3: Detection of Herpes Viruses

Figure 7:
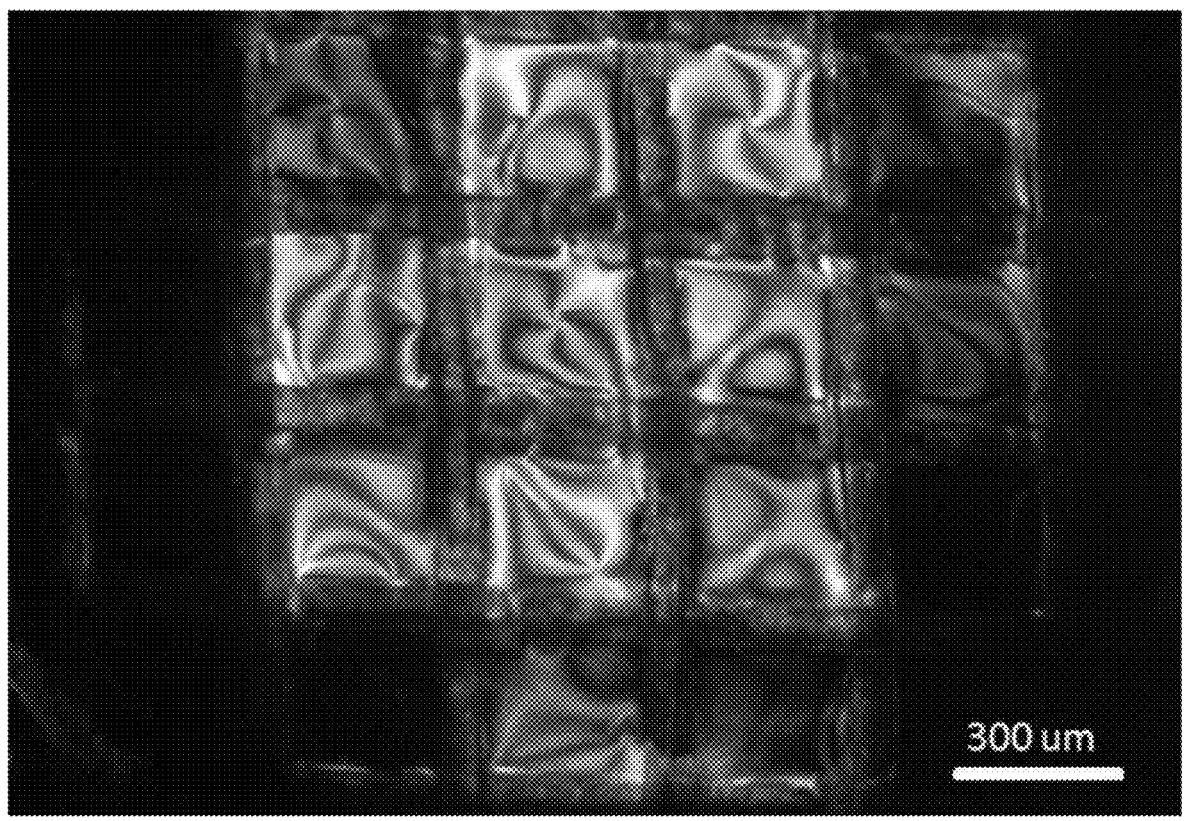
FIG. 7 illustrates a polarized image captured from thermotropic HSV-1 viruses placed on an impregnated fabric with LCs utilizing a polarized light microscope, consistent with one or more exemplary embodiments of the present disclosure.

Detection of herpes viruses was performed using a method similar to method 400 and using a system similar to system 100. A confluent monolayer of Baby Hamster Kidney fibroblasts (BHK) cells prepared in plates were infected with herpes simplex virus type 1 (HSV-1) strain KOS at a multiplicity of infection of $1\times107$ PFU/ml. The cells were infected with HSV-1 for 48 hours at 37° C. The cells were diluted for preparing different concentrations of HSV-1 infected viruses. A negative sample was also prepared for comparison. DNA of viruses were analyzed utilizing aDNA, RNA, protein quantitation spectrophotometer device. As used herein, a DNA, RNA, protein quantitation spectrophotometer is a device that measures light absorbance by nucleic acids and purified proteins in a sample and calculate the concentration of nucleic acids and purified proteins in the sample. To impregnate a silk fabric, 0.1 μL of the prepared sample was added on the fabric. After passing a light beam through a first polarizer similar to first polarizer 110, the light beam was refracted due to orientations of LCs in contact with HSV-1. The refracted light beam passed through a second polarizer similar to second polarizer 114 and a pattern was captured for the sample. A processor similar to processing unit 118 converted the pattern into vectors and compared the data with reference vectors. The processor identified HSV-1 due to a resemblance of the vectors of the sample to the reference vectors of HSV-1 stored in the memory of the processor. The processor detected HSV-1 samples by measuring similarity of more than 80% between the vectors of the sample and the vectors of the reference sample. Exemplary reference samples were prepared based on various concentrations of HSV-1. Therefore, concentrations of HSV-1 sample can be measured according to the similarity factor of more than 80% between the vectors of the HSV-1 sample and the vectors of a reference sample of the plurality of reference samples. FIG. 7 illustrates a polarized image captured from thermotropic HSV-1 viruses placed on an impregnated fabric with LCs utilizing a polarized light microscope, consistent with one or more exemplary embodiments of the present disclosure.

Example 4: Detection of Methanol in Alcoholic Liquids

Figure 8A:
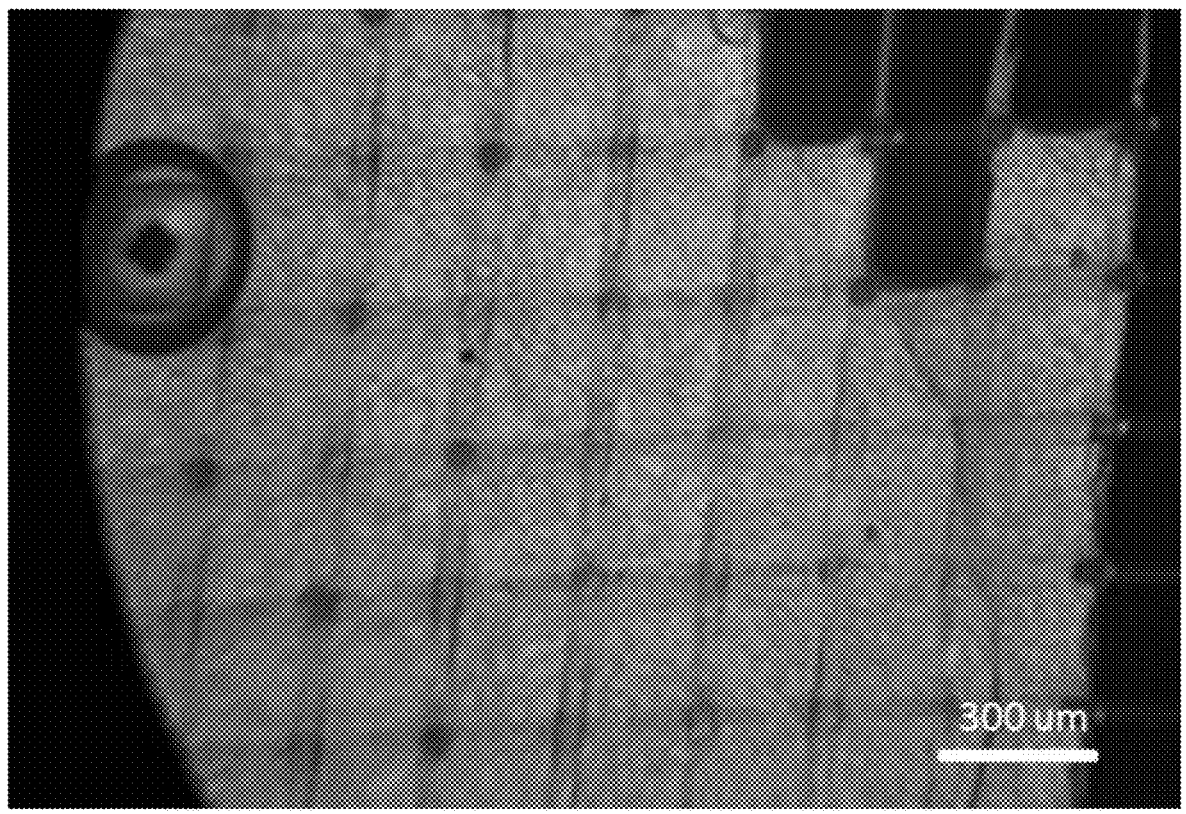
FIG. 8A illustrates a polarized image captured from LCs in a fabric moisturized with red wine as a biological medium placed on the LCs before illumination utilizing a polarized light microscope, consistent with one or more exemplary embodiments of the present disclosure.
Figure 8B:
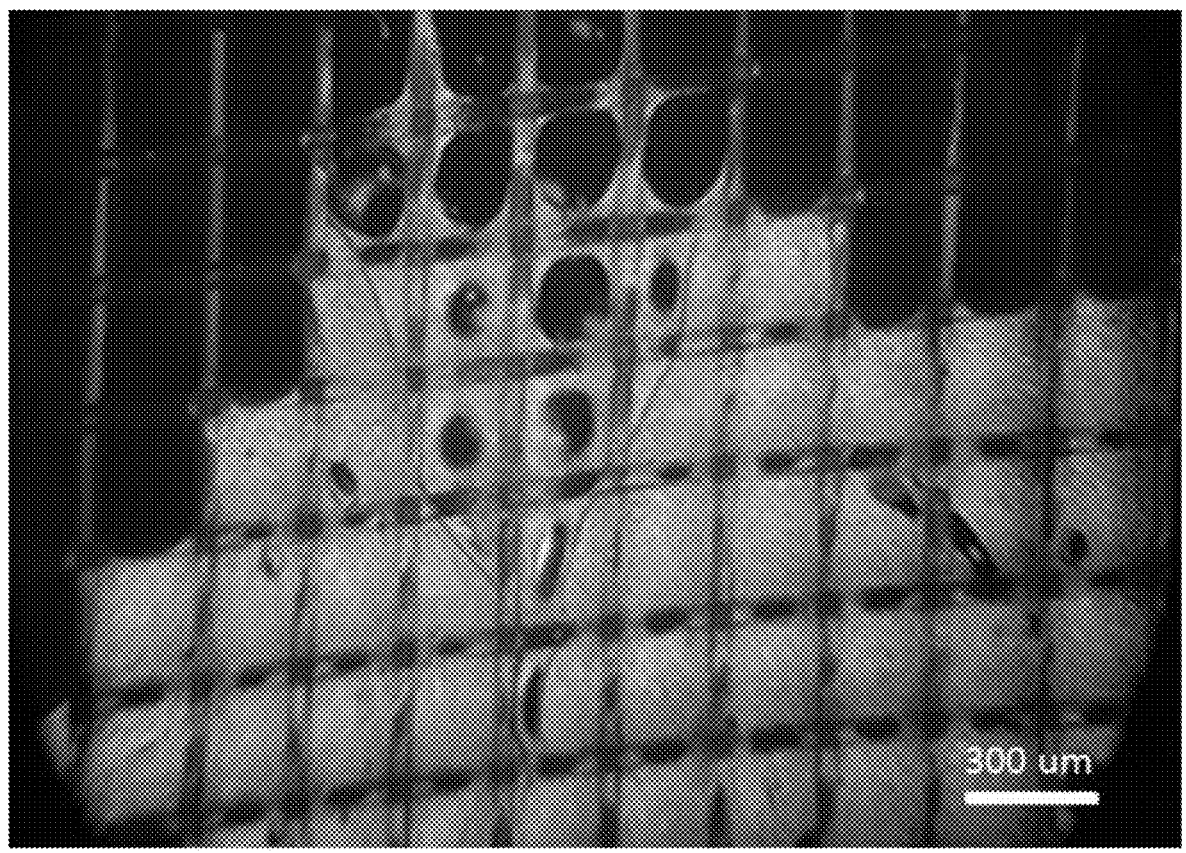
FIG. 8B illustrates a polarized image captured from LCs in a fabric with a mixture of 98 wt. % red wine and 2 wt. % methanol placed on the LCs before illumination, consistent with one or more exemplary embodiments of the present disclosure.
Figure 8C:
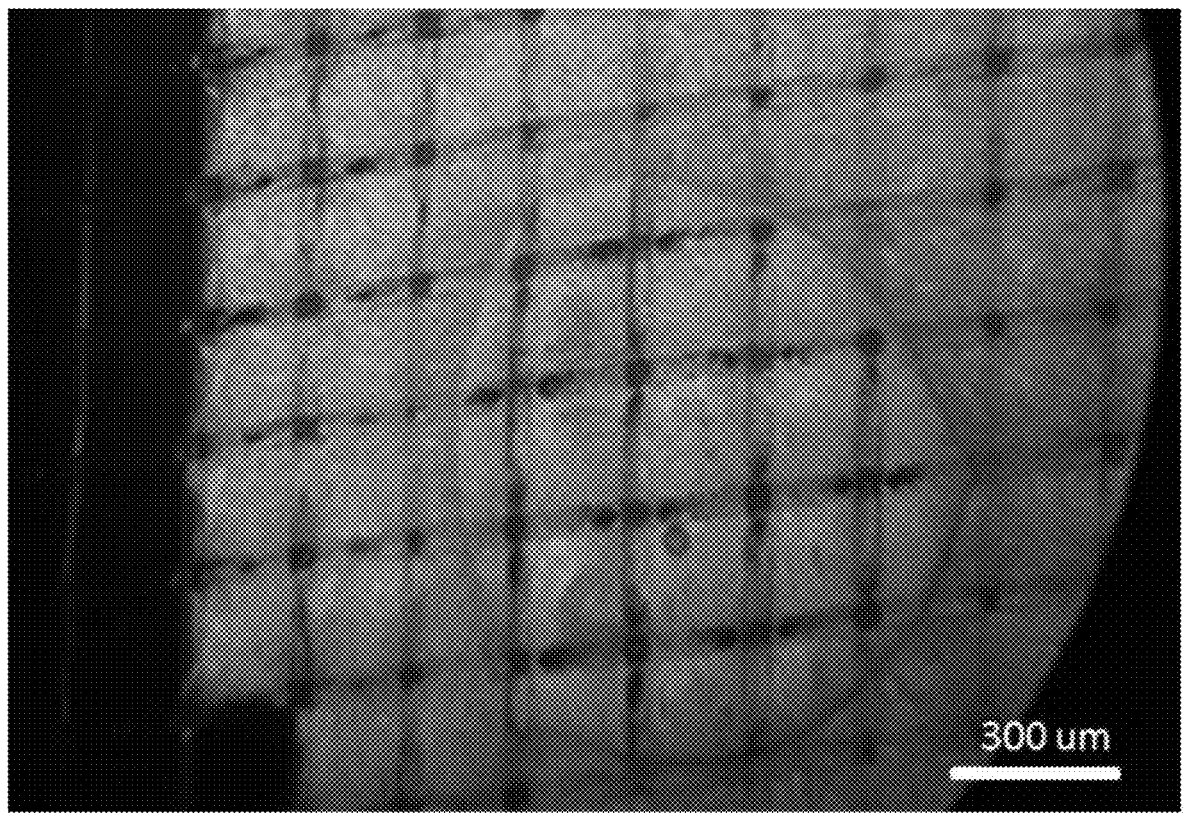
FIG. 8C illustrates a polarized image captured from LCs in a fabric with a mixture of 96 wt. % red wine and 4 wt. % methanol placed on the LCs before illumination utilizing a polarized light microscope, consistent with one or more exemplary embodiments of the present disclosure.
Figure 8D:
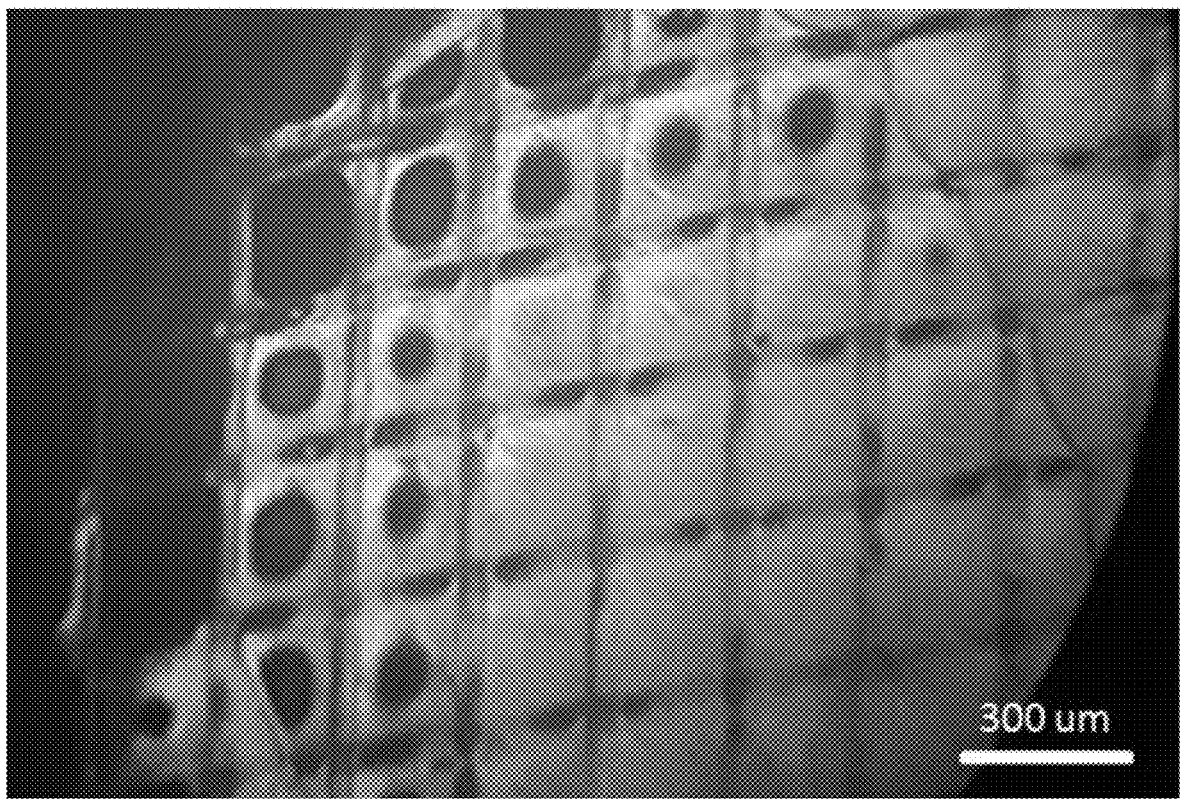
FIG. 8D illustrates a polarized image captured from LCs in a fabric with a mixture of 94 wt. % red wine and 6 wt. % methanol placed on the LCs before illumination utilizing a polarized light microscope, consistent with one or more exemplary embodiments of the present disclosure.
Figure 8E:
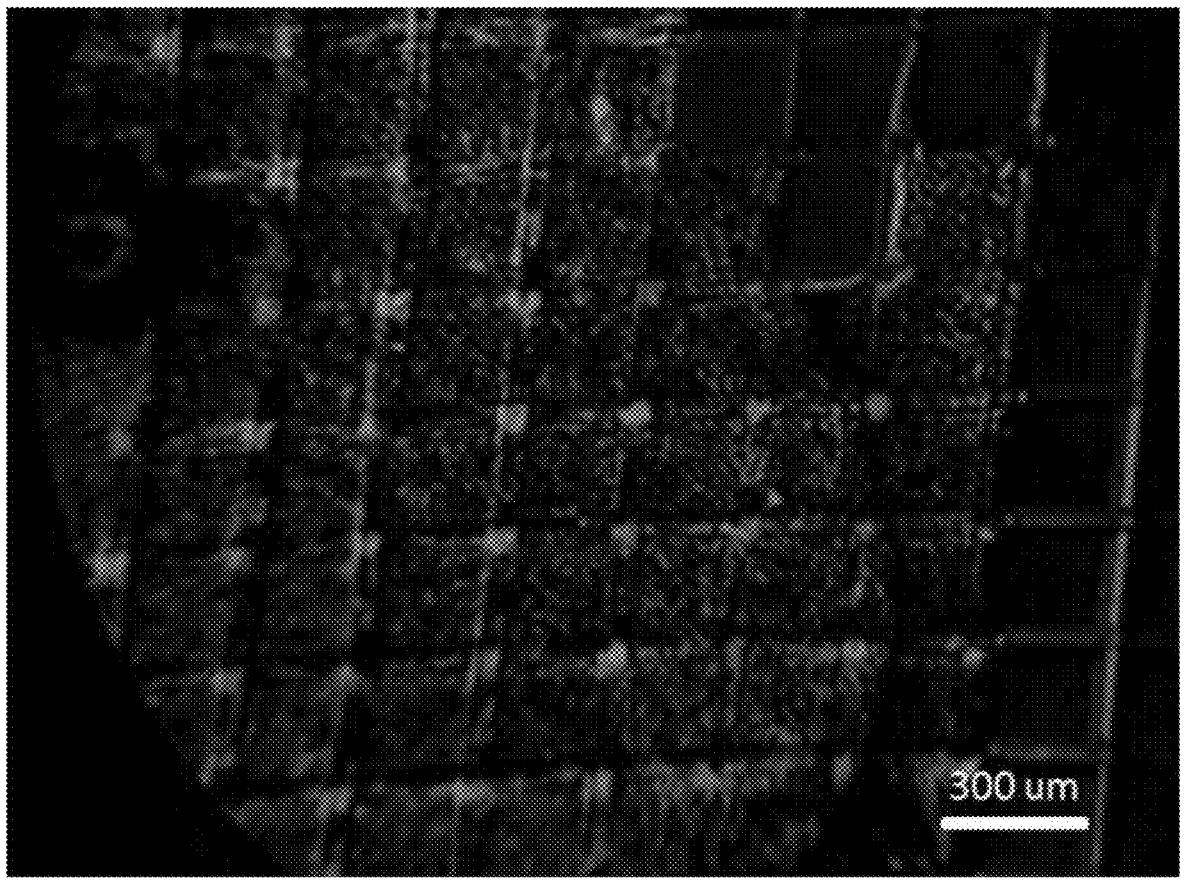
FIG. 8E illustrates a polarized image captured from LCs in a fabric with red wine as a biological medium placed on the LCs after illumination utilizing a polarized light microscope, consistent with one or more exemplary embodiments of the present disclosure.
Figure 8F:
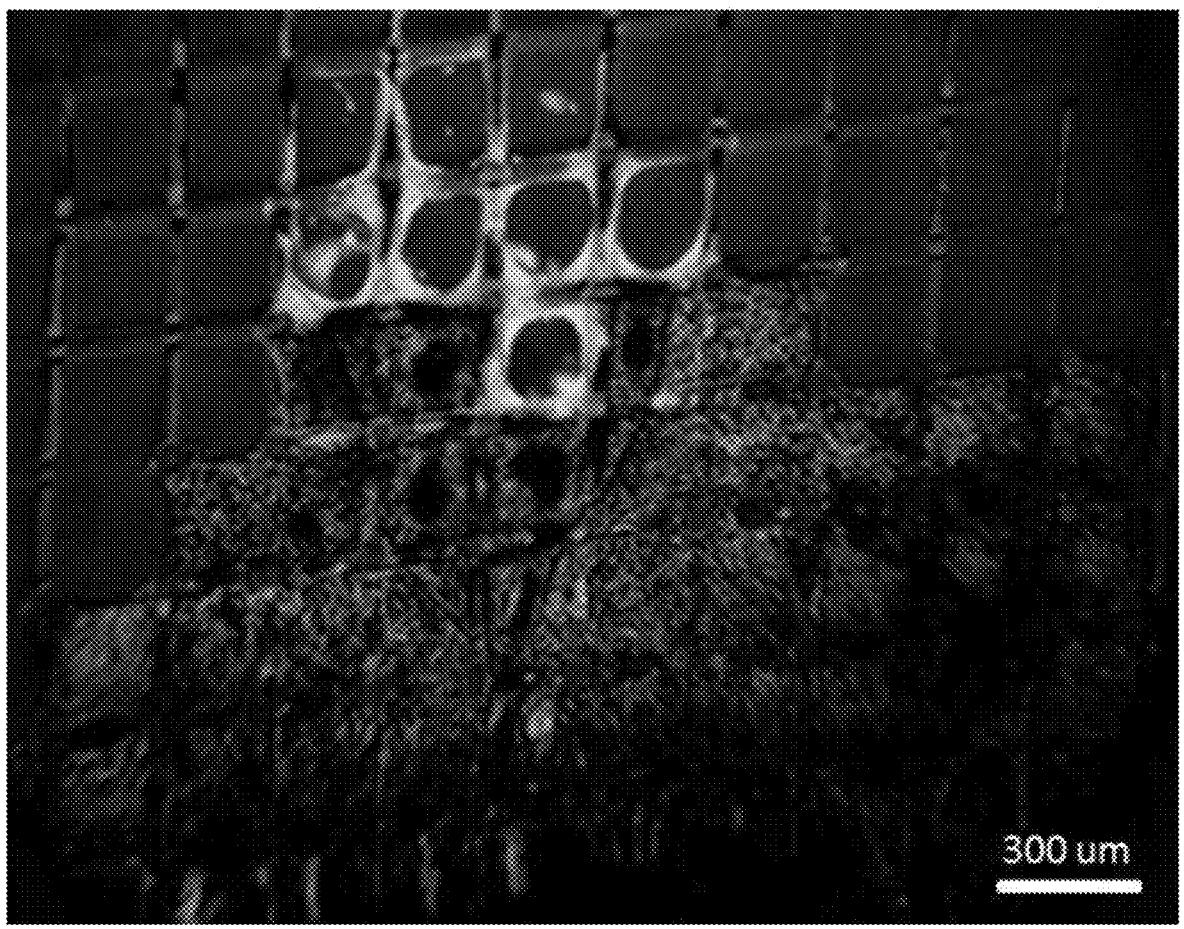
FIG. 8F illustrates a polarized image captured from LCs in a fabric with a mixture of 98 wt. % red wine and 2 wt. % methanol placed on the LCs after illumination utilizing a polarized light microscope, consistent with one or more exemplary embodiments of the present disclosure.
Figure 8G:
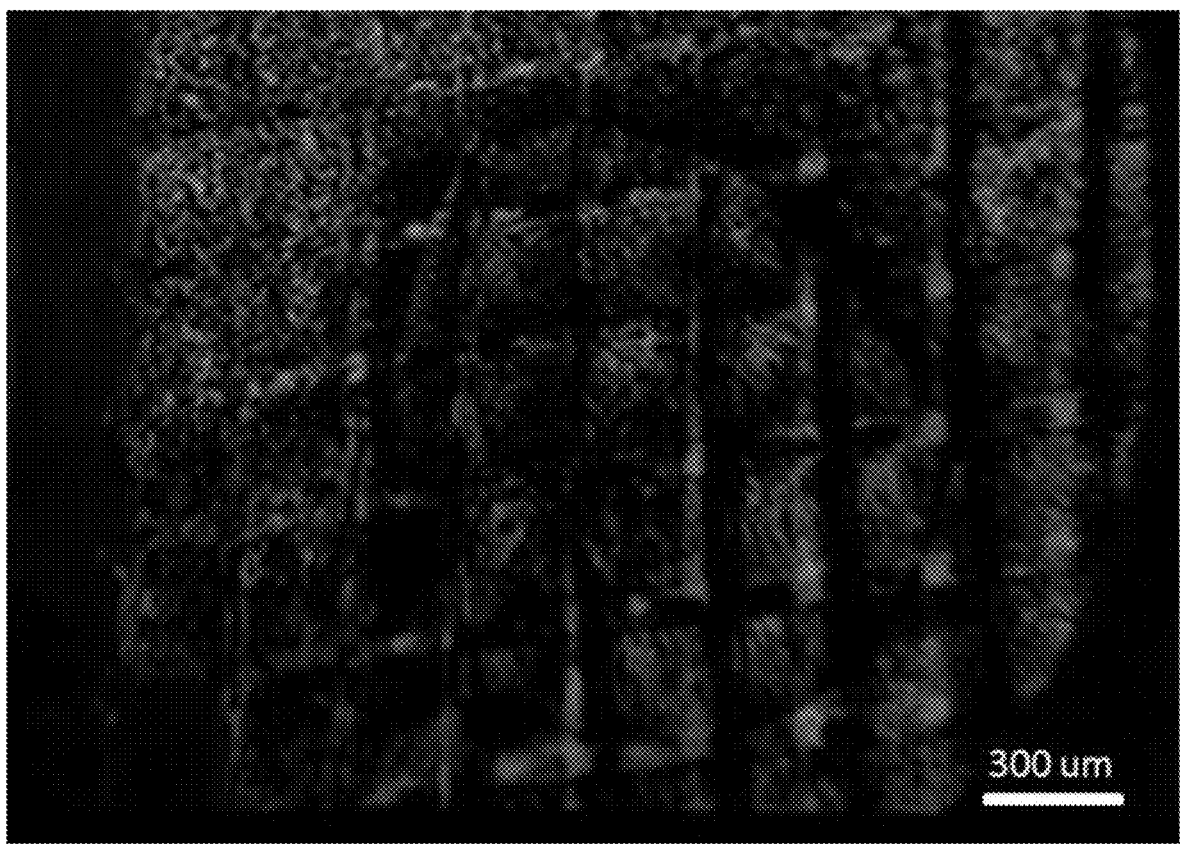
FIG. 8G illustrates a polarized image captured from LCs in a fabric with a mixture of 96 wt. % red wine and 4 wt. % methanol on the LCs after illumination utilizing a polarized light microscope, consistent with one or more exemplary embodiments of the present disclosure.
Figure 8H:
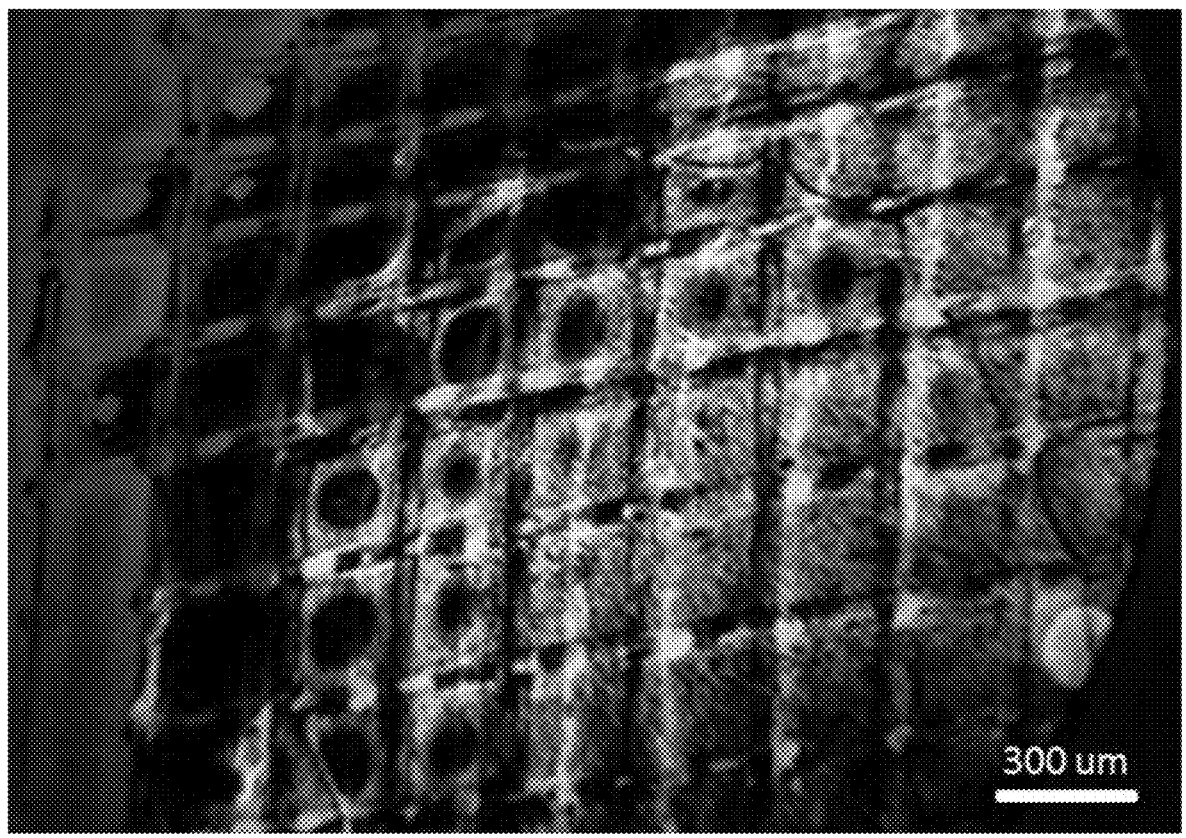
FIG. 8H illustrates a polarized image captured from LCs in a fabric with a mixture of 94 wt. % red wine and 6 wt. % methanol on the LCs after illumination utilizing a polarized light microscope, consistent with one or more exemplary embodiments of the present disclosure.
Figure 9A:
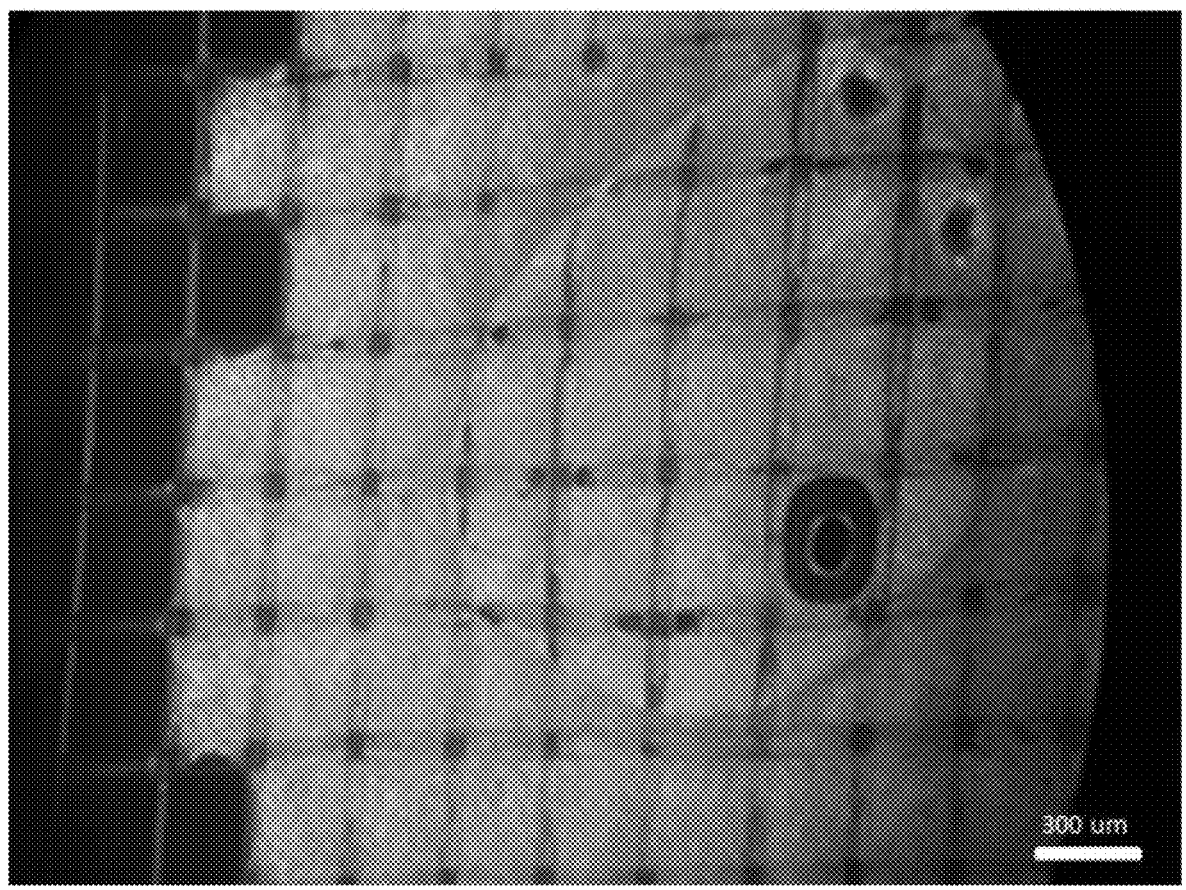
FIG. 9A illustrates a polarized image captured from vodka on an impregnated fabric with LCs before illumination utilizing a polarized light microscope, consistent with one or more exemplary embodiments of the present disclosure.
Figure 9B:
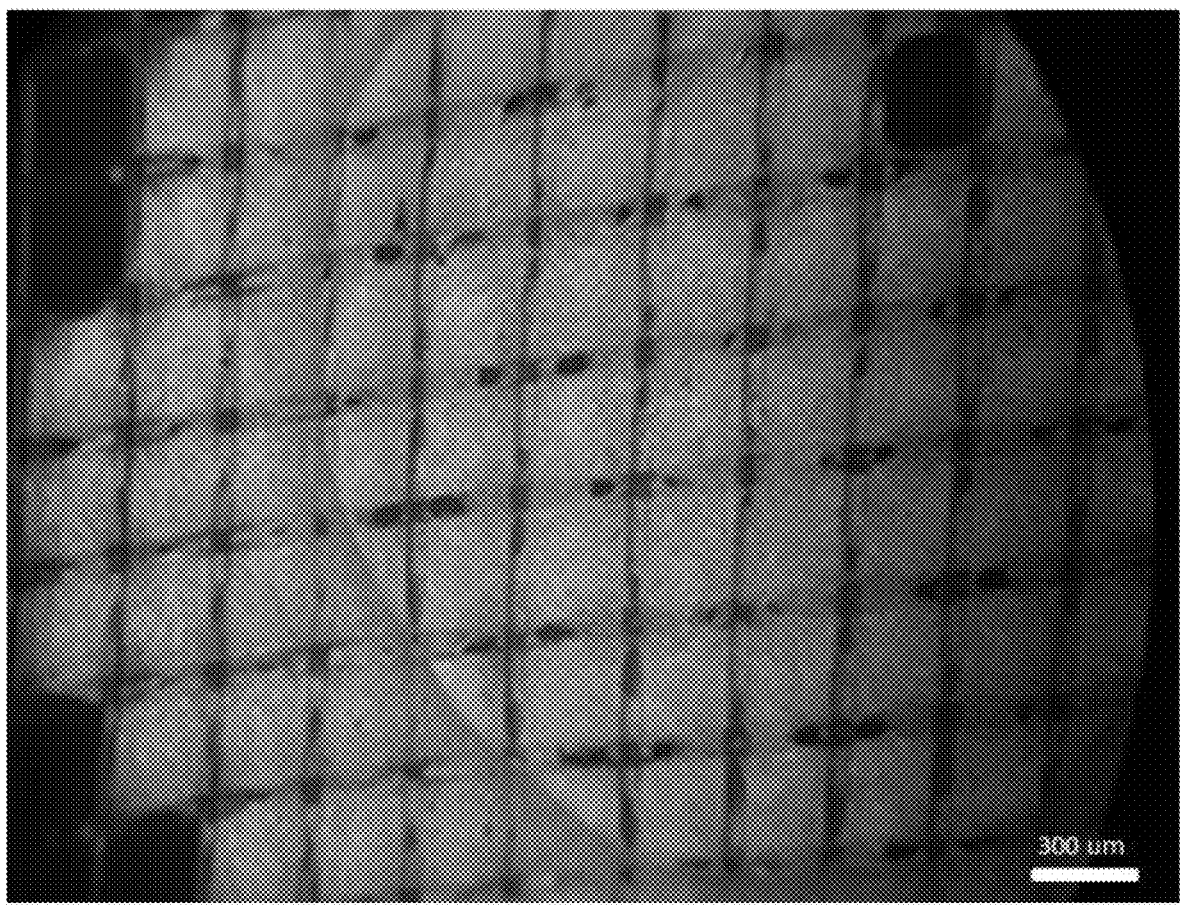
FIG. 9B illustrates a polarized image captured from 98 wt. % vodka and 2 wt. % methanol on an impregnated fabric with LCs before illumination utilizing a polarized light microscope, consistent with one or more exemplary embodiments of the present disclosure.
Figure 9C:
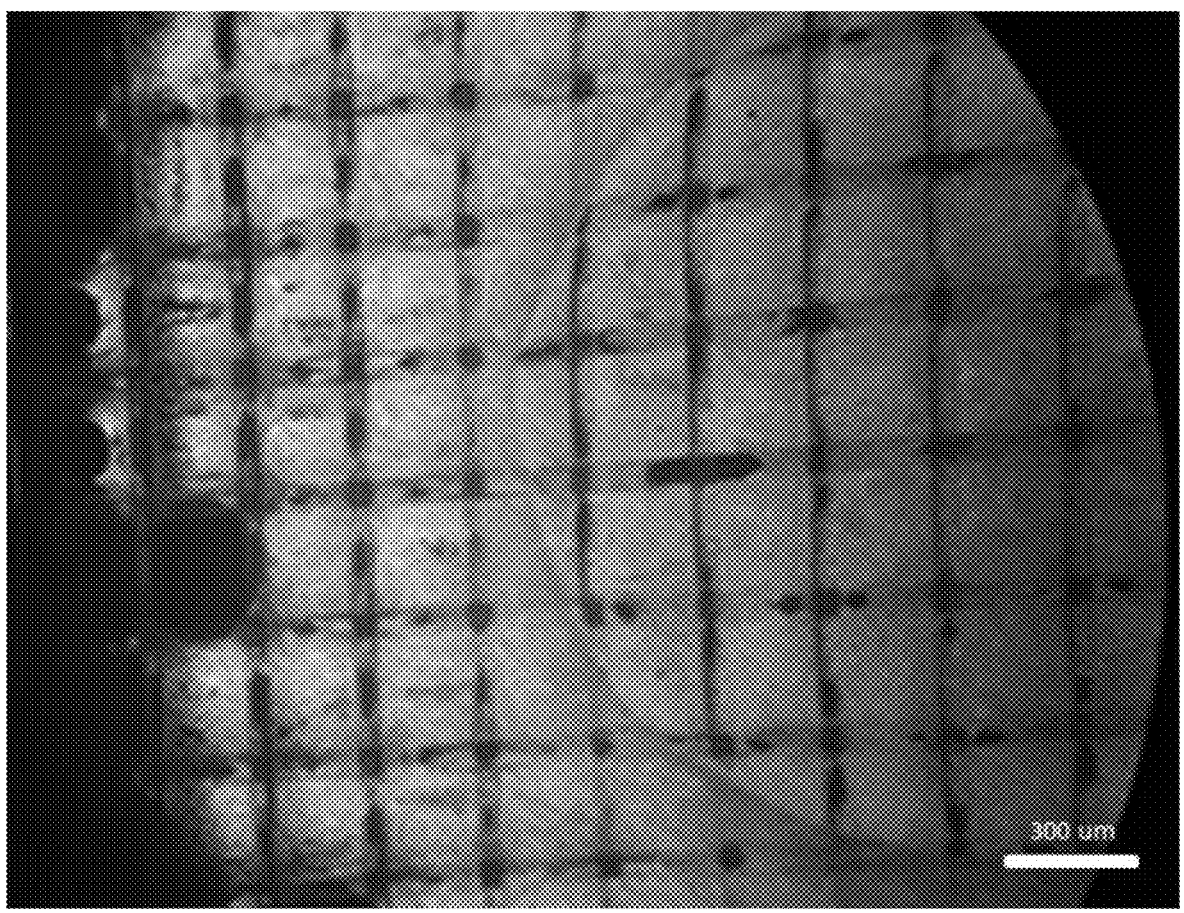
FIG. 9C illustrates a polarized image captured from 96 wt. % vodka and 4 wt. % methanol on an impregnated fabric with LCs before illumination utilizing a polarized light microscope, consistent with one or more exemplary embodiments of the present disclosure.
Figure 9D:
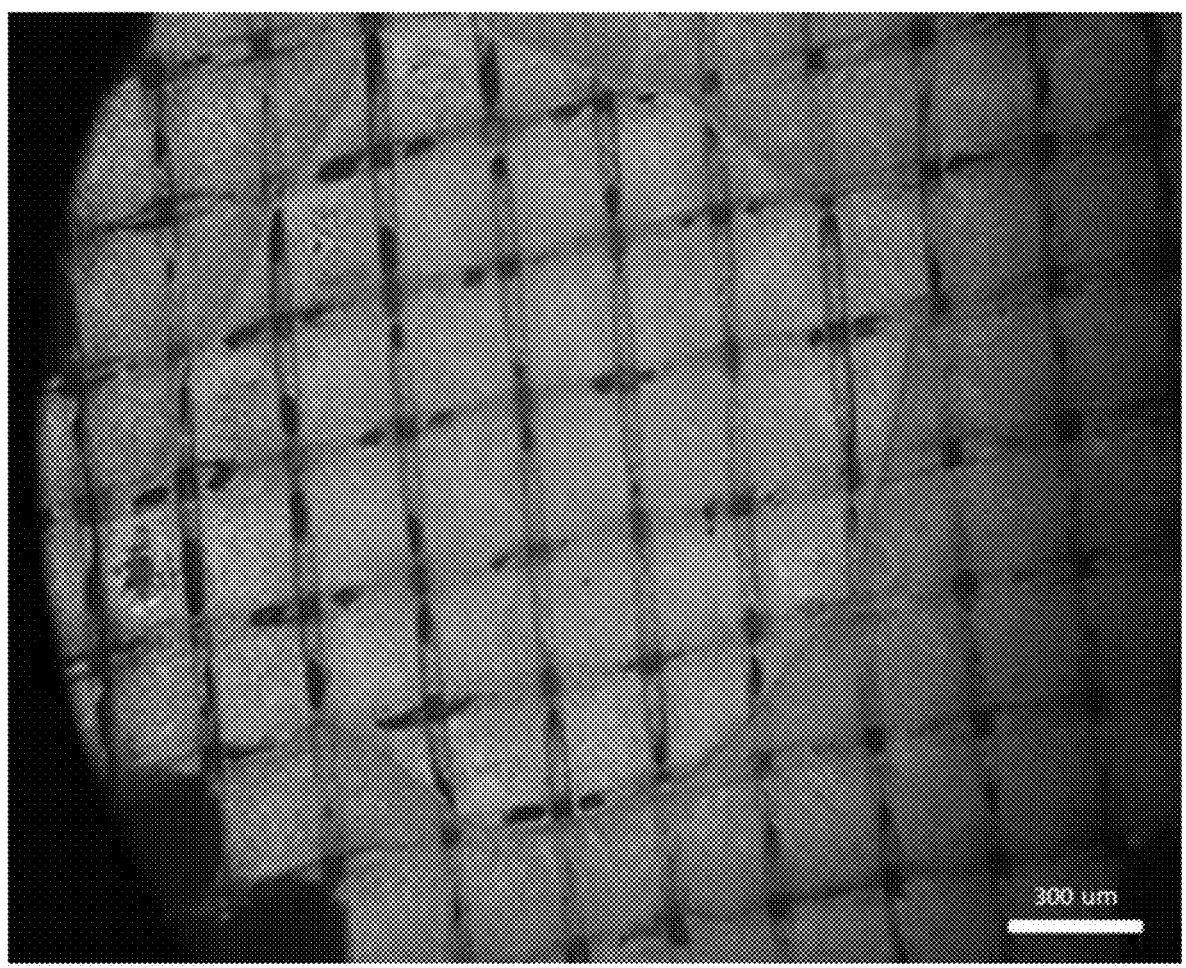
FIG. 9D illustrates a polarized image captured from 94 wt. % vodka and 6 wt. % methanol on an impregnated fabric with LCs before illumination utilizing a polarized light microscope, consistent with one or more exemplary embodiments of the present disclosure.
Figure 9E:
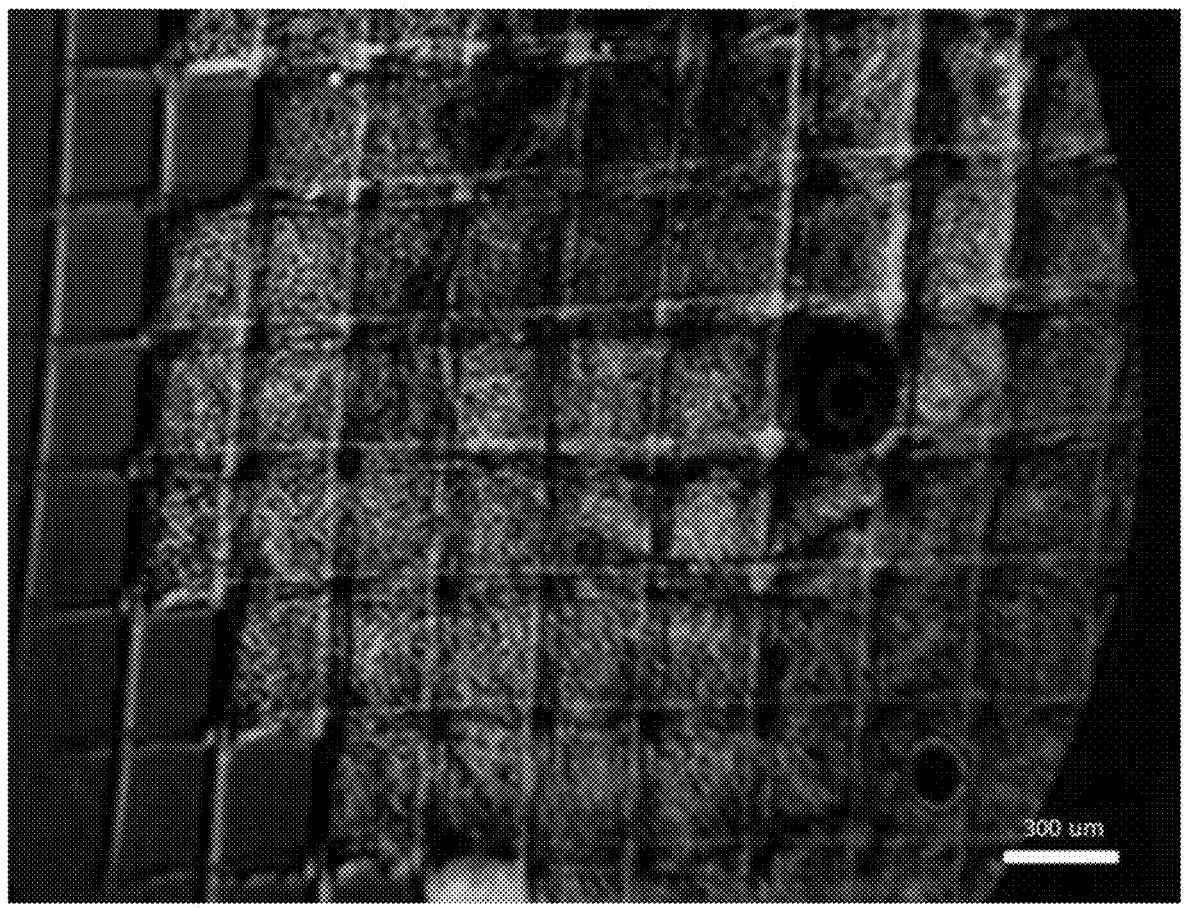
FIG. 9E illustrates a polarized image captured from vodka as a biological medium on an impregnated fabric with LCs after illumination utilizing a polarized light microscope, consistent with one or more exemplary embodiments of the present disclosure.
Figure 9F:
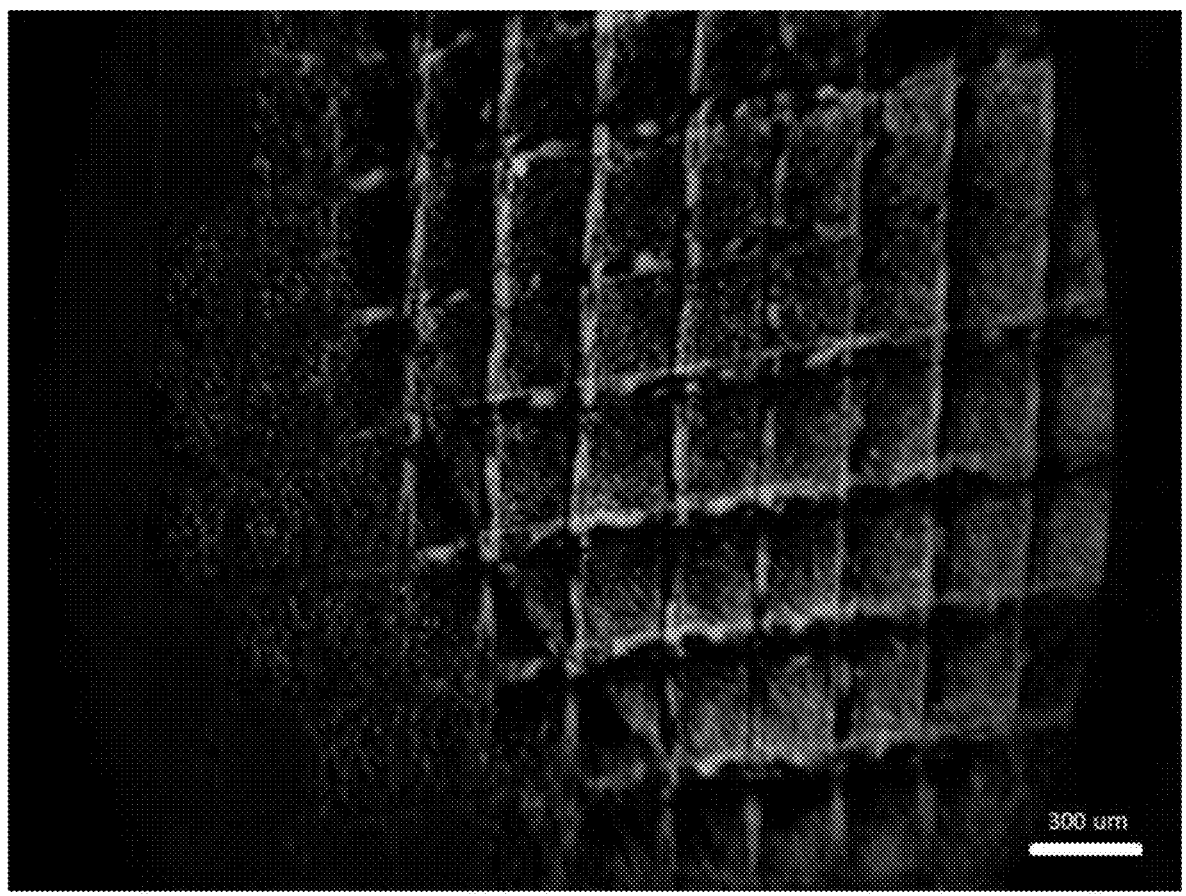
FIG. 9F illustrates a polarized image captured from 98 wt. % vodka and 2 wt. % methanol on an impregnated fabric with LCs after illumination utilizing a polarized light microscope, consistent with one or more exemplary embodiments of the present disclosure.
Figure 9G:
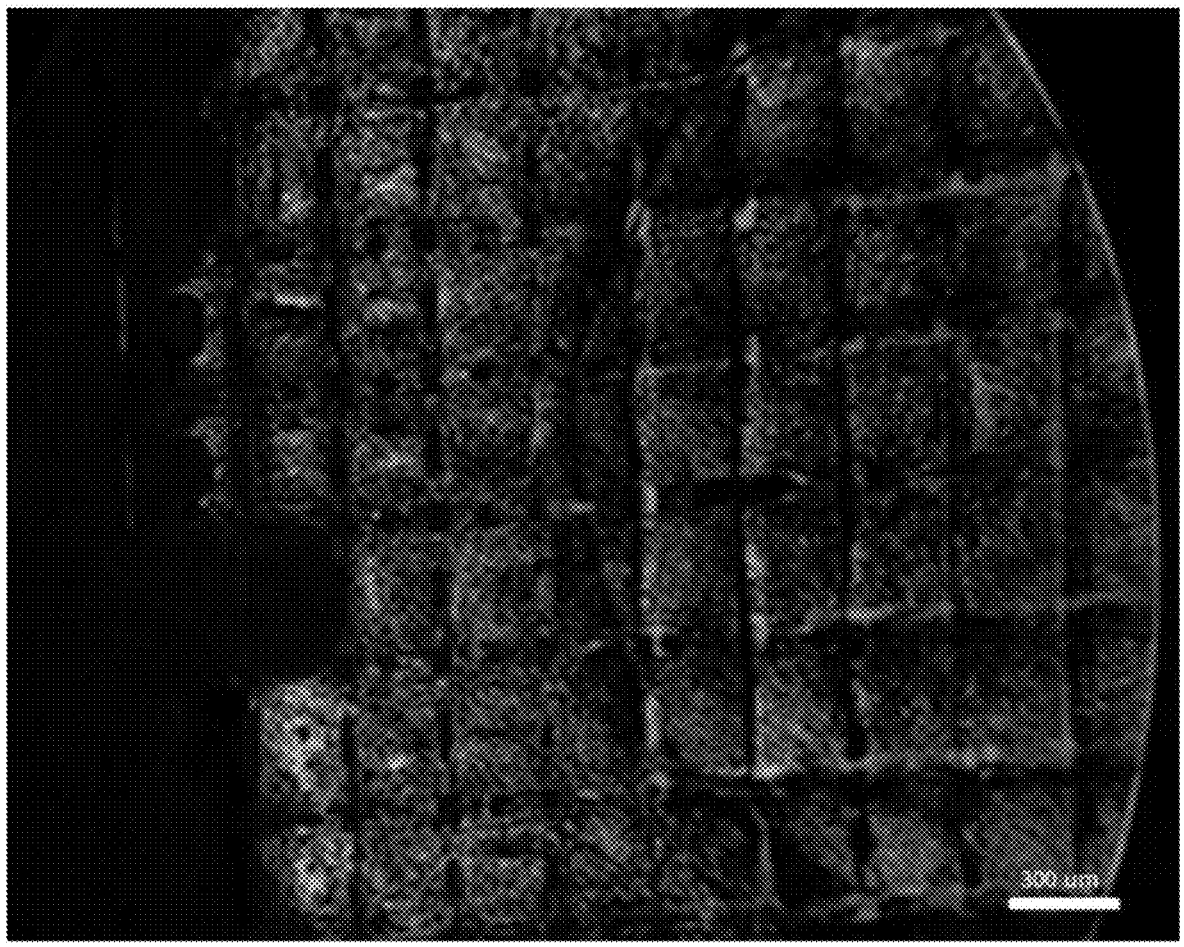
FIG. 9G illustrates a polarized image captured from 96 wt. % vodka and 4 wt. % methanol on an impregnated fabric with LCs after illumination utilizing a polarized light microscope, consistent with one or more exemplary embodiments of the present disclosure.
Figure 9H:
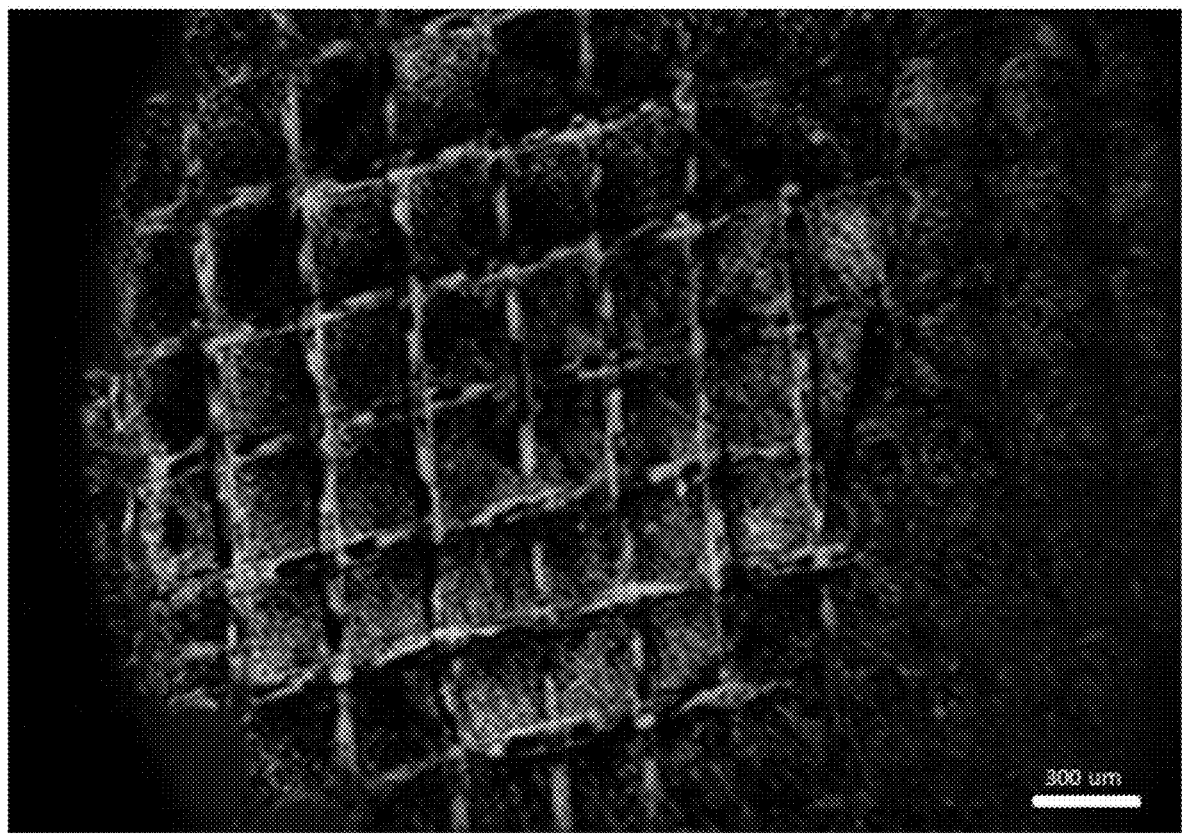
FIG. 9H illustrates a polarized image captured from 94 wt. % vodka and 6 wt. % methanol on an impregnated fabric with LCs after illumination utilizing a polarized light microscope, consistent with one or more exemplary embodiments of the present disclosure.

Detection of methanol in alcoholic liquids was performed using a method similar to method 400 and using a system similar to system 100. To this end, methanol was added to several chiral nematic LCs (CLCs) in which the LCs include E7 and BDH1305 as a chiral dopant. A silk fabric was impregnated with CLCs. A mixture of red wine and 0 wt. %, 2 wt. %, 4 wt. %, and 6 wt. % of methanol was added on the fabric impregnated with CLCs. Different concentrations of methanol can form respective patterns with various color intensities. As a concentration of methanol increased, color intensity of an associated formed pattern was enhanced. Data of multiple reference samples with various concentrations of methanol were stored in a processer similar to processing unit 118 for comparison with pattern formed by a sample containing an unknown amount of methanol to detect a presence/absence of methanol therein and determine an exact amount of methanol. FIG. 8A illustrates a polarized image captured from LCs in a fabric moisturized with red wine as a biological medium placed on the LCs before illumination utilizing a polarized light microscope, consistent with one or more exemplary embodiments of the present disclosure. FIG. 8B illustrates a polarized image captured from LCs in a fabric with a mixture of 98 wt. % red wine and 2 wt. % methanol placed on the LCs before illumination, consistent with one or more exemplary embodiments of the present disclosure. FIG. 8C illustrates a polarized image captured from LCs in a fabric with a mixture of 96 wt. % red wine and 4 wt. % methanol placed on the LCs before illumination utilizing a polarized light microscope, consistent with one or more exemplary embodiments of the present disclosure. FIG. 8D illustrates a polarized image captured from LCs in a fabric with a mixture of 94 wt. % red wine and 6 wt. % methanol placed on the LCs before illumination utilizing a polarized light microscope, consistent with one or more exemplary embodiments of the present disclosure. FIG. 8E illustrates a polarized image captured from LCs in a fabric with red wine as a biological medium placed on the LCs after illumination utilizing a polarized light microscope, consistent with one or more exemplary embodiments of the present disclosure. FIG. 8F illustrates a polarized image captured from LCs in a fabric with a mixture of 98 wt. % red wine and 2 wt. % methanol placed on the LCs after illumination utilizing a polarized light microscope, consistent with one or more exemplary embodiments of the present disclosure. FIG. 8G illustrates a polarized image captured from LCs in a fabric with a mixture of 96 wt. % red wine and 4 wt. % methanol on the LCs after illumination utilizing a polarized light microscope, consistent with one or more exemplary embodiments of the present disclosure. FIG. 8H illustrates a polarized image captured from LCs in a fabric with a mixture of 94 wt. % red wine and 6 wt. % methanol on the LCs after illumination utilizing a polarized light microscope, consistent with one or more exemplary embodiments of the present disclosure. The patterns after illumination were processed and differences in methanol concentration in the samples were detectable. The same procedure was performed for vodka with 0 wt. %, 2 wt. %, 4 wt. %, and 6 wt. % of methanol. FIG. 9A illustrates a polarized image captured from vodka on an impregnated fabric with LCs before illumination utilizing a polarized light microscope, consistent with one or more exemplary embodiments of the present disclosure. FIG. 9B illustrates a polarized image captured from 98 wt. % vodka and 2 wt. % methanol on an impregnated fabric with LCs before illumination utilizing a polarized light microscope, consistent with one or more exemplary embodiments of the present disclosure. FIG. 9C illustrates a polarized image captured from 96 wt. % vodka and 4 wt. % methanol on an impregnated fabric with LCs before illumination utilizing a polarized light microscope, consistent with one or more exemplary embodiments of the present disclosure. FIG. 9D illustrates a polarized image captured from 94 wt. % vodka and 6 wt. % methanol on an impregnated fabric with LCs before illumination utilizing a polarized light microscope, consistent with one or more exemplary embodiments of the present disclosure. FIG. 9E illustrates a polarized image captured from vodka as a biological medium on an impregnated fabric with LCs after illumination utilizing a polarized light microscope, consistent with one or more exemplary embodiments of the present disclosure. FIG. 9F illustrates a polarized image captured from 98 wt. % vodka and 2 wt. % methanol on an impregnated fabric with LCs after illumination utilizing a polarized light microscope, consistent with one or more exemplary embodiments of the present disclosure. FIG. 9G illustrates a polarized image captured from 96 wt. % vodka and 4 wt. % methanol on an impregnated fabric with LCs after illumination utilizing a polarized light microscope, consistent with one or more exemplary embodiments of the present disclosure. FIG. 9H illustrates a polarized image captured from 94 wt. % vodka and 6 wt. % methanol on an impregnated fabric with LCs after illumination utilizing a polarized light microscope, consistent with one or more exemplary embodiments of the present disclosure.

Example 5: Detection of Vases

Figure 10A:
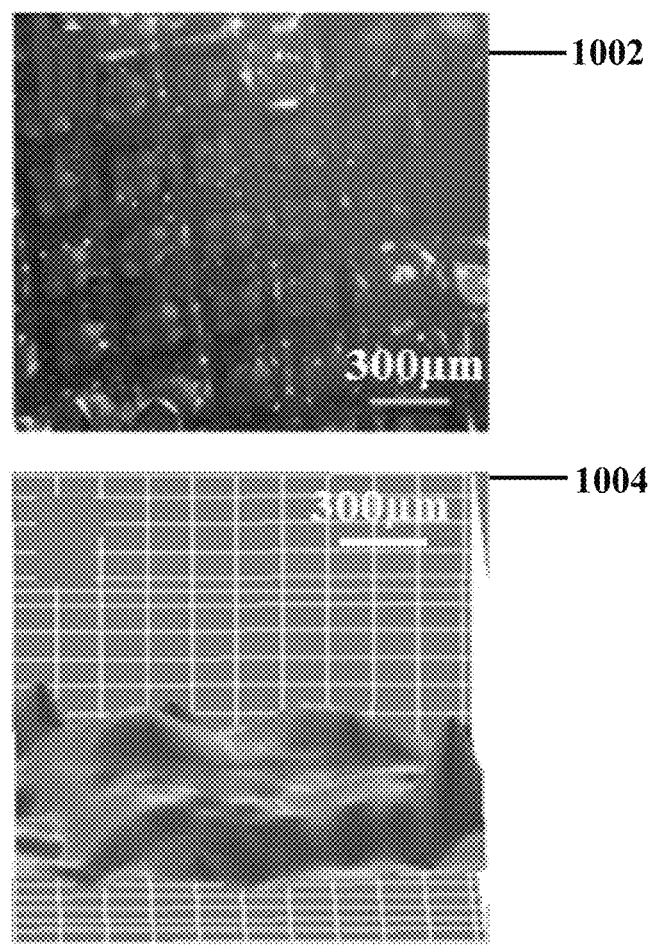
FIG. 10A illustrates a polarized image captured from LCs in the fabric with a flow of air over the LCs utilizing a polarized light microscope, consistent with one or more exemplary embodiments of the present disclosure.
Figure 10B:
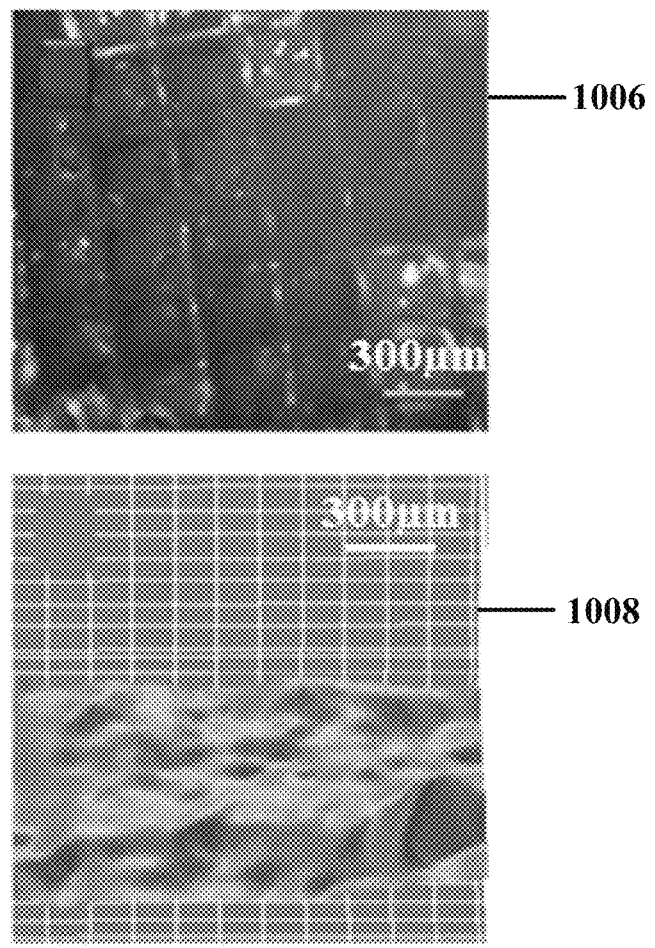
FIG. 10B illustrates a polarized image captured from LCs in the fabric with a flow of $CO_2$ over the LCs utilizing a polarized light microscope, consistent with one or more exemplary embodiments of the present disclosure.
Figure 10C:
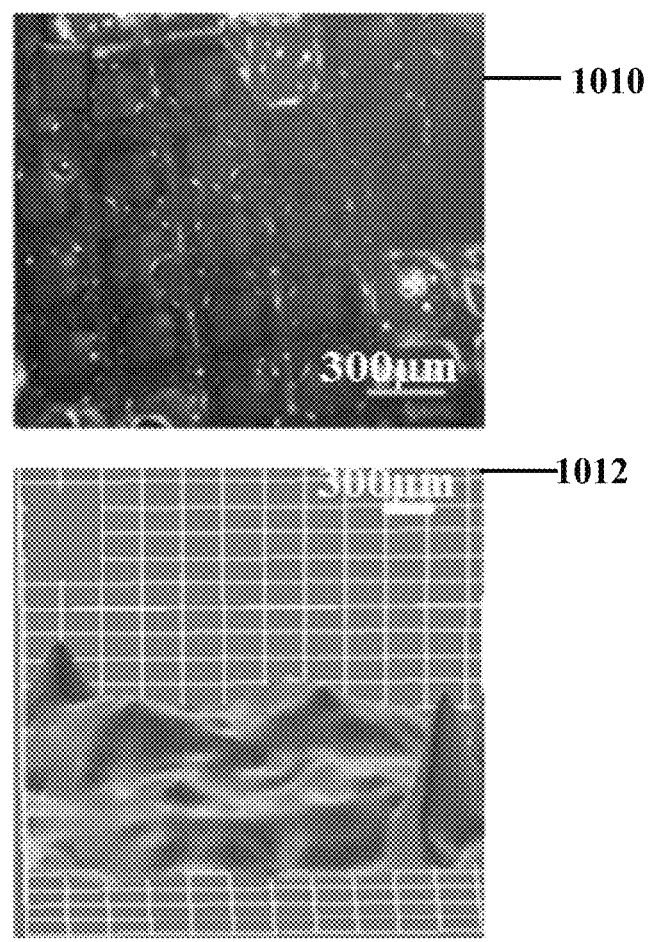
FIG. 10C illustrates a polarized image captured from LCs in the fabric after withdrawal of $CO_2$ utilizing a polarized light microscope, consistent with one or more exemplary embodiments of the present disclosure.
Figure 11:
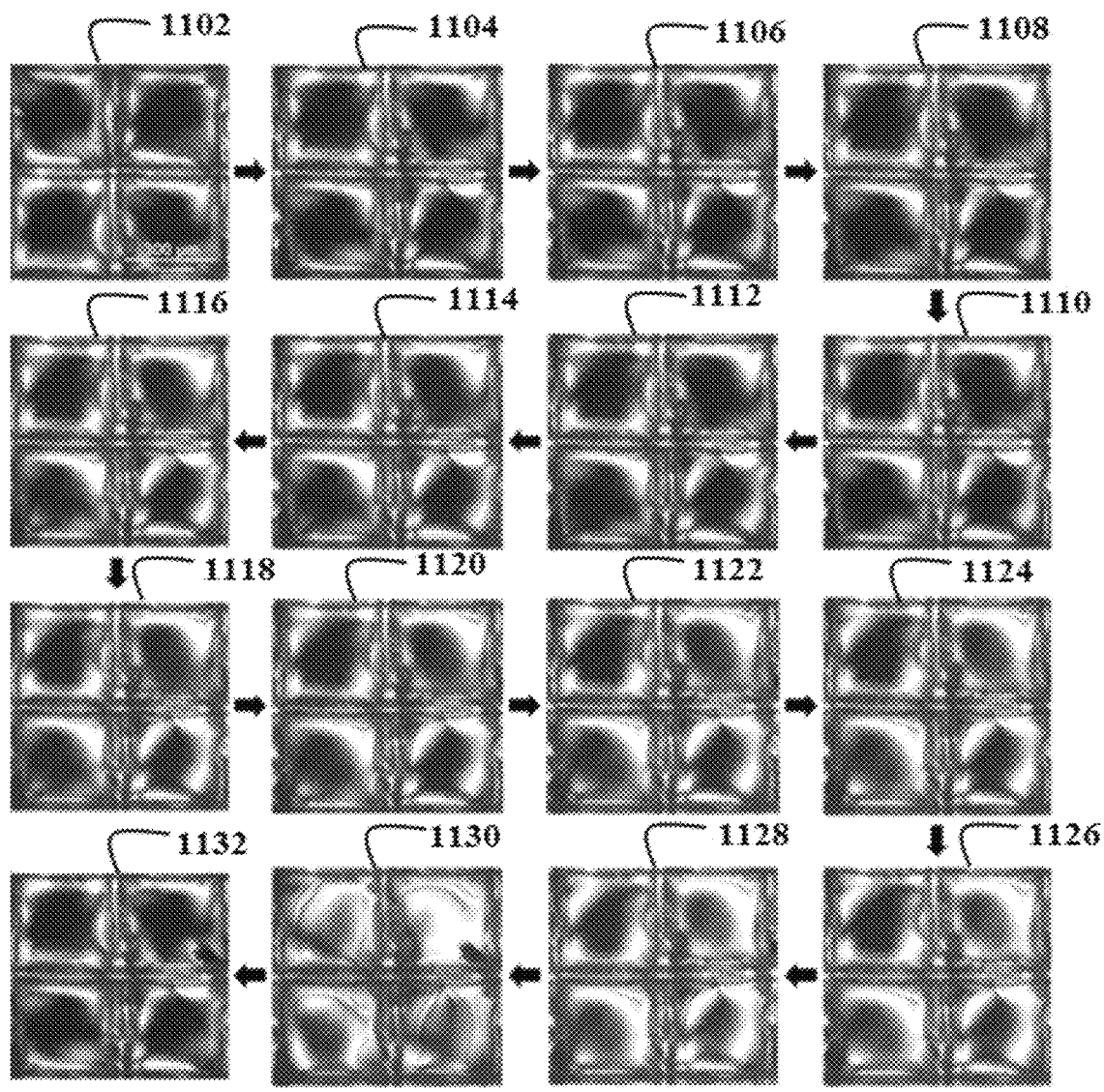
FIG. 11 illustrates polarized images captured from LCs in the fabric after purging $CO_2$ with different velocities utilizing a polarized light microscope, consistent with one or more exemplary embodiments of the present disclosure.

Detection of gases was performed using a method similar to method 400 and using a system similar to system 100. LCs of E7 were mixed with diethanolamine and a silk fabric was impregnated with the mixture of LCs and diethanolamine. The fabric was placed inside a gas chamber with 1000 ppm of $CO_2$ passing on the fabric. LCs' orientation changed after 5 minutes of passing $CO_2$. After gas purging, air was injected inside the chamber and the orientation of the LCs returned to the original state. The volumetric flow of the gases was measured utilizing a rotameter. The orientation of the LCs varies with the variations in the flow velocity. After passing a light beam through a first polarizer similar to first polarizer 110, the light beam was refracted due to orientations of LCs in contact with $CO_2$. The refracted light beam passed through a second polarizer similar to second polarizer 114 and a pattern was captured for $CO_2$ sample. A processor similar to processing unit 118 converted the pattern into vectors and compared the data with reference vectors. The processor identified $CO_2$ due to their resemblance to the reference vectors of $CO_2$ stored in memory of the processor. The processor detected $CO_2$ samples by measuring similarity of more than 80% between the vectors of the $CO_2$ sample and the vectors of a reference sample of a plurality of reference samples. Exemplary reference patterns were formed according to various velocities of $CO_2$. Therefore, a velocity of $CO_2$ sample was detected based on the similarity factor of more than 80% between a reference sample of the plurality of reference samples and the $CO_2$ sample. FIG. 10A illustrates a polarized image captured from LCs in the fabric with a flow of air over the LCs utilizing a polarized light microscope, consistent with one or more exemplary embodiments of the present disclosure. Image 1002 shows impregnated fabric with LCs after flow of air. Image 1004 shows image processing of image 1002 utilizing a machine learning technique. FIG. 10B illustrates a polarized image captured utilizing a polarized light microscope of LCs in the fabric with a flow of $CO_2$ over the LCs, consistent with one or more exemplary embodiments of the present disclosure. Image 1006 shows impregnated fabric with LCs after flow of $CO_2$. Image 1008 shows image processing of image 1006 utilizing a machine learning technique. FIG. 10C illustrates a polarized image captured from LCs in the fabric after withdrawal of $CO_2$ utilizing a polarized light microscope, consistent with one or more exemplary embodiments of the present disclosure. Image 1010 shows impregnated fabric with LCs after withdrawing $CO_2$. Image 1012 shows image processing of image 1010 utilizing a machine learning technique. FIG. 11 illustrates polarized images captured from LCs in the fabric after purging $CO_2$ with different velocities utilizing a polarized light microscope, consistent with one or more exemplary embodiments of the present disclosure. Images 1102, 1104, 1106, 1108, 1110, 1112, 1114, 1116, 1118, 1120, 1122, 1124, 1126, 1128, 1130, and 1132 show patterns of the impregnated fabric with LCs after purging 0 L/M (lit/minute), 0.5 L/M, 1 L/M, 1.5 L/M, 2 L/M, 2.5 L/M, 3 L/M, 3.5 L/M, 4

Figure 12:
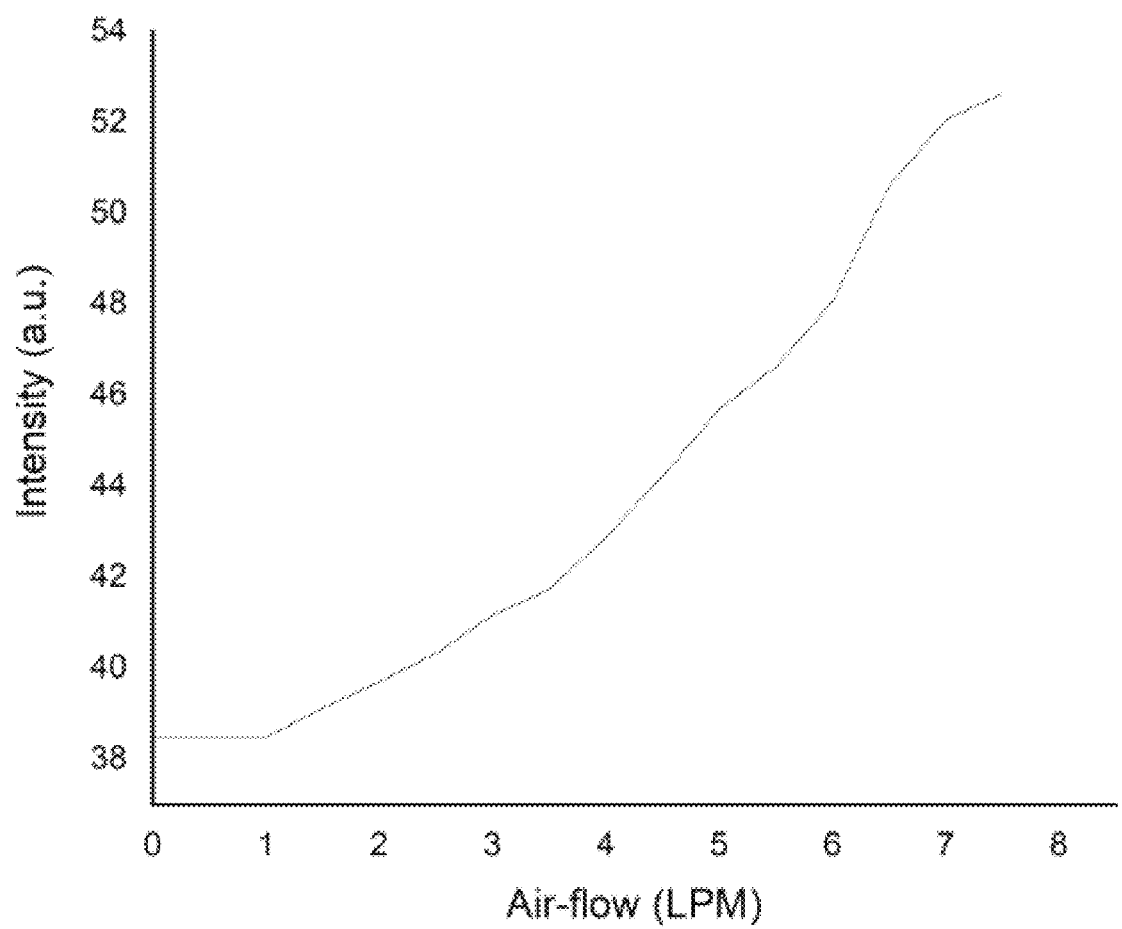
FIG. 12 illustrates absorbance intensity diagram of an impregnated fabric with LCs after purging $CO_2$ with different velocities, consistent with one or more exemplary embodiments of the present disclosure.

L/M, 4.5 L/M, 5 L/M, 5.5 L/M, 6 L/M, 6.5 L/M, 7 L/M, 7.5 L/M, and 0 L/M of $CO_2$ respectively. Different velocities of $CO_2$ can form a pattern with various color intensities so that color intensity of the pattern is enhanced by increasing a velocity of $CO_2$. Data of multiple velocities of $CO_2$ including patterns formed by orientations of LCs for a plurality of reference samples with different $CO_2$ velocities were stored in a processer similar to processing unit 118 for comparison with a pattern in the presence of an unknown sample to detect a presence or absence of $CO_2$ in the unknown sample. FIG. 12 illustrates absorbance intensity diagram of an impregnated fabric with LCs after purging $CO_2$ with different velocities, consistent with one or more exemplary embodiments of the present disclosure.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A system for detecting a target material in a sample, comprising:
    a sensor configured to hold the sample placed thereon, the sensor comprising:
        a fabric comprising an array of pixels, each respective pixel of the array of pixels comprising a square hole formed by texture of the fabric; and
        liquid crystals (LCs) impregnated into the array of pixels;
    a light source;
    an image-capturing device;
    two linear crossed polarizers; comprising:
        a first polarizer placed between the light source and the sensor; and
        a second polarizer placed between the sensor and the image-capturing device; and
    a processing unit electrically connected to the light source and the image-capturing device, the processing unit comprising:
        a memory having processor-readable instructions stored therein; and
        a processor configured to access the memory and execute the processor-readable instructions, which, when executed by the processor configures the processor to perform a method, the method comprising:
            transmitting, utilizing the light source, a light beam through a path comprising the first polarizer, the sensor, and the second polarizer;
            capturing, utilizing the image-capturing device, an image from a surface of the second polarizer, the image comprising a pattern formed by orientations of the LCs; and detecting a presence of the target material in the sample by analyzing the pattern formed by orientations of the LCs.

2. The system of claim 1, wherein analyzing the pattern formed by orientations of the LCs comprises:
comparing the pattern formed by orientations of the LCs with a set of reference patterns of the target material; and
detecting the presence of the target material in the sample responsive to the pattern formed by orientations of the LCs being similar to a reference pattern of the set of reference patterns with a similarity of more than 80%, the similarity of more than 80% comprising orientations of the LCs associated with at least 80% pixels of the array of pixels being the same in the pattern formed by orientations of the LCs and the reference pattern.

3. The system of claim 2, wherein the set of reference patterns of the target material comprises a set of images captured from the surface of the second polarizer respective to a set of formed orientations of the LCs responsive to placing a respective set of reference samples containing a respective set of amounts of the target material on the sensor.

4. The system of claim 3, wherein analyzing the pattern formed by orientations of the LCs comprises:
generating an array of vectors for each reference pattern of the set of reference patterns by determining a direction for each respective vector corresponding to an orientation of LCs in a respective pixel of the array of pixels based on a color spectrum of the respective pixel in the reference pattern;
generating a sample array of vectors for the pattern formed by orientations of LCs in the sample by determining a direction for each respective vector corresponding to an orientation of LCs in a respective pixel of the array of pixels based on a color spectrum of the respective pixel in the pattern formed by orientations of LCs in the sample;
comparing the sample array of vectors with the array of vectors of each reference pattern of the set of reference patterns; and
determining the presence of the target material in the sample responsive to a direction of each vector of the sample array of vectors being the same to a direction of each respective vector of the array of vectors of a first reference pattern of the set of reference patterns.

5. The system of claim 4, wherein analyzing the pattern formed by orientations of the LCs further comprises determining an amount of the target material in the sample by determining the amount of the target material in the sample equal to a first amount of the target material of the set of amounts of the target material, the first reference pattern being corresponding to a reference sample containing the first amount of the target material.

6. The system of claim 1, wherein each pixel of the plurality of pixels comprises a square piece of the fabric with a dimension in a range of 1 μm to 600 μm.

7. The system of claim 1, wherein analyzing the pattern formed by orientations of the LCs comprises analyzing the pattern formed by orientations of the LCs after placing the sample on the sensor for a time period in a range of 10 seconds to 10 minutes.

8. The system of claim 1, wherein the fabric has a thickness in a range of 10 μm to 100 μm.

9. The system of claim 1, wherein the sensor comprises LCs with a volume in a range of 0.0001 μL to 0.0005 μL impregnated into each pixel of the array of pixels.

10. The system of claim 1, wherein the fabric is made of at least one of polyester, rayon, linen, nylon, silk, and combinations thereof.

11. The system of claim 1, wherein each pixel of the array of pixels comprises a volume in a range of 0.0001 μL to 0.003 μL of the sample placed on the sensor.

12. The system of claim 1, wherein the first polarizer and the second polarizer are linear crossed polarizers.

13. The system of claim 12, wherein the first polarizer has 90 degree difference in light transmittance respective to the second polarizer.

14. The system of claim 1, wherein:
a distance between the first polarizer and the sensor is less than 15 cm; and
a distance between the second polarizer and the sensor is in a range of 0.2 cm to 30 cm.

15. The system of claim 1, wherein transmitting the light beam comprises transmitting the light beam with a wavelength within a range of UV-Visible wavelength.

16. The system of claim 1, wherein LCs impregnated into the array of pixels comprises at least one of thermotropic LCs, lyotropic LCs, and combinations thereof.

17. The system of claim 16, wherein the thermotropic LCs comprises at least one of nematic LCs, smectic LCs, chiral phases, twisted nematic LCs, discotic LCs, conic LCs, and combinations thereof.

18. The system of claim 1, wherein the sensor further comprises a holder placed around the fabric, the holder is made of at least one of iron, galvanized steel, polymethylmethacrylate, wood, and combinations thereof.

19. The system of claim 1, wherein the sensor further comprises a binding agent added to each respective pixel of the array of pixels, the binding agent configured to interact with the target material in the sample, the binding agent comprising at least one of diethanolamine, hexavalent vaccine, pentavalent vaccine, aptamers, and combinations thereof.

20. The system of claim 1, wherein:
the sample comprises one of a sputum sample, a blood sample, and a nasal mucosa sample acquired from a person suspected to be infected by COVID-19 virus; and
detecting the presence of the target material in the sample by analyzing the pattern formed by orientations of the LCs comprises detecting a COVID-19 infection in the sample by analyzing the pattern formed by orientations of the LCs.

* * * * *